(12) United States Patent
Yanagawa

(10) Patent No.: US 11,543,409 B2
(45) Date of Patent: Jan. 3, 2023

(54) SENSOR SUBSTRATE, DETECTION DEVICE, AND MANUFACTURING METHOD OF SENSOR SUBSTRATE

(71) Applicant: Panasonic Intellectual Property Management Co., Ltd., Osaka (JP)

(72) Inventor: Hiroto Yanagawa, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 442 days.

(21) Appl. No.: 16/749,314

(22) Filed: Jan. 22, 2020

(65) Prior Publication Data

US 2020/0158723 A1 May 21, 2020

Related U.S. Application Data

(63) Continuation of application No. PCT/JP2018/035059, filed on Sep. 21, 2018.

(30) Foreign Application Priority Data

Oct. 4, 2017 (JP) .............................. JP2017-194171

(51) Int. Cl.
*G01N 21/65* (2006.01)
*G01N 21/64* (2006.01)
(Continued)

(52) U.S. Cl.
CPC ........ *G01N 33/54366* (2013.01); *B01L 3/502* (2013.01); *B82Y 15/00* (2013.01);
(Continued)

(58) Field of Classification Search
None
See application file for complete search history.

(56) References Cited

U.S. PATENT DOCUMENTS 5,955,729 A * 9/1999 Nelson ................. G01N 21/553
250/423 P
2010/0041065 A1 2/2010 Horii et al.
(Continued)

FOREIGN PATENT DOCUMENTS

EP 1286187 2/2003
JP 2000-055920 2/2000
(Continued)

OTHER PUBLICATIONS

International Search Report of PCT application No. PCT/JP2018/035059 dated Dec. 18, 2018.
(Continued)

*Primary Examiner* — Neil N Turk
(74) *Attorney, Agent, or Firm* — McDermott Will & Emery LLP

(57) ABSTRACT

The present disclosure provides a sensor substrate capable of detecting a trace amount of an analyte. This sensor substrate according to the present disclosure is a sensor substrate comprising a metal microstructure that generates surface plasmon when irradiated with excitation light. The metal microstructure is composed of a plurality of protrusions disposed in a planar shape. The plurality of the protrusions are disposed in such a manner that imaginary lines V each passing through a center between adjacent protrusions draw a honeycomb shape in a plan view. Each of the plurality of the protrusions has a substantially hexagonal shape in the plan view. A depth in a thickness direction of the sensor substrate of a gap present between the adjacent protrusions is larger than a radius of an imaginary circle inscribed in a hexagon forming the honeycomb shape.

8 Claims, 22 Drawing Sheets

(51) Int. Cl.
*G01N 33/543* (2006.01)
*B82Y 15/00* (2011.01)
*B82Y 20/00* (2011.01)
*B01L 3/00* (2006.01)

(52) U.S. Cl.
CPC ............ *B82Y 20/00* (2013.01); *G01N 21/648* (2013.01); *G01N 21/6428* (2013.01); *G01N 21/65* (2013.01); *G01N 21/658* (2013.01); *B01L 2200/12* (2013.01); *B01L 2300/0627* (2013.01); *B01L 2300/12* (2013.01); *G01N 2021/6439* (2013.01)

(56) References Cited

U.S. PATENT DOCUMENTS

| | | |
|---|---|---|
| 2011/0166045 A1 | 7/2011 | Dhawan et al. |
| 2015/0139856 A1 | 5/2015 | Yamada et al. |
| 2015/0212003 A1 | 7/2015 | Shibayama et al. |
| 2015/0233832 A1 | 8/2015 | Maruyama et al. |
| 2017/0052121 A1 | 2/2017 | Chen et al. |

FOREIGN PATENT DOCUMENTS

| | | |
|---|---|---|
| JP | 2007-240361 | 9/2007 |
| JP | 2008-025989 | 2/2008 |
| JP | 2008-128787 | 6/2008 |
| JP | 2008-196898 | 8/2008 |
| JP | 2010-043890 | 2/2010 |
| JP | 2010-043934 | 2/2010 |
| JP | 2013-231637 | 11/2013 |
| JP | 2014-037973 | 2/2014 |
| JP | 2015-014547 | 1/2015 |

OTHER PUBLICATIONS

Fung Suong Ou et al., "Hot-Spot Engineering in Polygonal Nanofinger Assemblies for Surface Enhanced Raman Spectroscopy", Nano Letters, May 23, 2011, vol. 11, pp. 2538-2542.

* cited by examiner

SENSOR SUBSTRATE, DETECTION DEVICE, AND MANUFACTURING METHOD OF SENSOR SUBSTRATE

BACKGROUND

1. Technical Field

The present disclosure relates to a sensor substrate for detecting an analyte (for example, a virus) in a sample, a detection device, and a manufacturing method of the sensor substrate.

2. Description of the Related Art

Conventionally, a fluorescence method has been widely used as a technique for detecting an analyte in a sample (see, for example, Patent Literature 1). In Patent Literature 1, first, an analyte to which an antibody labeled with a fluorescent substance (hereinafter, referred to as a labeled antibody) has been bound is bound onto a sensor part through an antibody immobilized on the sensor part including a metal layer (hereinafter, such an antibody is referred to as an immobilized antibody). Then, by irradiating the sensor part with excitation light, plasmon is excited on the metal layer, and a photoelectric field enhanced by the plasmon is generated. At this time, an amount of the analyte can be detected by measuring an amount of fluorescence generated from the fluorescent substance of the labeled antibody present in the enhanced photoelectric field (hereinafter, referred to as "enhanced electric field").

Patent Literature 2 discloses an optical device having a substrate having a dielectric on the surface thereof, a plurality of metal particles formed on the dielectric, and an organic molecular film that is formed on the dielectric between the metal particles and capable of causing a target molecule to adhere thereto. In Patent Literature 2, the organic molecular film is formed on the dielectric between the metal particles which are a hot site where the enhanced electric field is formed. Thereby, an optical signal can be detected by efficiently using the enhanced electric field. In addition, since a gap between adjacent metal particles is formed widely at an entrance side of the target molecule, the probability that the target molecule is adsorbed to the organic molecular film while increasing the enhanced electric field by narrowing the gap between the metal particles can be increased.

Patent Literature 3 discloses a plasmon resonance structure in which a plurality of metal fine protrusions each having an outer surface part formed of a metal material are periodically arranged on a substrate. In Patent Literature 3, the plurality of the metal fine protrusions are formed to be tapered along a height direction perpendicular to a principal surface of the substrate, and the metal fine protrusions are connected by a flat part having a flat exposed surface formed of a metal material. Such a configuration allows a generation position and electric field intensity of plasmon resonance on the surface of the metal fine protrusion to be easily controlled.

CITATION LIST

Patent Literature

Patent Literature 1: Japanese Patent Application Publication No. 2010-043934

Patent Literature 2: Japanese Patent Application Publication No. 2013-231637

Patent Literature 3: Japanese Patent Application Publication No. 2008-196898

SUMMARY

However, since concentration of virus floating in the air is much smaller than concentration of virus contained in the nasal discharge of a virus-infected patient, an amount of an analyte derived from the virus collected from the air is very small. Therefore, it is desired to detect a trace amount of an analyte.

The present disclosure provides a sensor substrate, a detection device, and a manufacturing method of the sensor substrate, with or by which a trace amount of an analyte is allowed to be detected.

The present disclosure provides a sensor substrate comprising:

a metal microstructure for generating surface plasmon when irradiated with excitation light, wherein the metal microstructure is composed of a plurality of protrusions disposed in a planar shape;

the plurality of the protrusions are disposed in such a manner that imaginary lines each passing through a center between adjacent protrusions included in the plurality of the protrusions draw a honeycomb shape in a plan view;

each of the plurality of the protrusions has a substantially hexagonal shape in the plan view; and a depth in a thickness direction of the sensor substrate of a gap present between the adjacent protrusions is larger than a radius of an imaginary circle inscribed in a hexagon forming the honeycomb shape.

The present disclosure also provides a detection device comprising:

the sensor substrates;

wherein a first antibody having a property of binding specifically to an analyte is immobilized on the metal microstructure of the sensor substrate;

the detection device further comprises:

an introduction opening through which a second antibody and a sample pass to the metal microstructure; wherein the second antibody has a property of binding specifically to the analyte and is labeled with a fluorescent substance, and wherein the sample may include the analyte;

a light irradiation part for irradiating the metal microstructure to which the second antibody and the sample has been introduced with the excitation light; and a detection part which detects the analyte based on fluorescence generated from the fluorescent substance by the irradiation with the excitation light.

In addition, the present disclosure also provides a manufacturing method of a sensor substrate comprising a metal microstructure for generating surface plasmon when irradiated with excitation light, the method comprising:

preparing a resin substrate having a plurality of fine protrusions; and forming a metal film on the resin substrate to form the sensor substrate comprising the metal microstructure having a plurality of protrusions, wherein the plurality of the protrusions are disposed in such a manner that imaginary lines each passing through a center between adjacent protrusions draw a honeycomb shape in a plan view;

each of the plurality of the protrusions has a substantially hexagonal shape in the plan view, and a depth in a thickness direction of the sensor substrate of a gap present between the adjacent protrusions is larger than a radius of an imaginary circle inscribed in a hexagon forming the honeycomb shape.

According to the present disclosure, a trace amount of an analyte can be detected.

Figure 1:
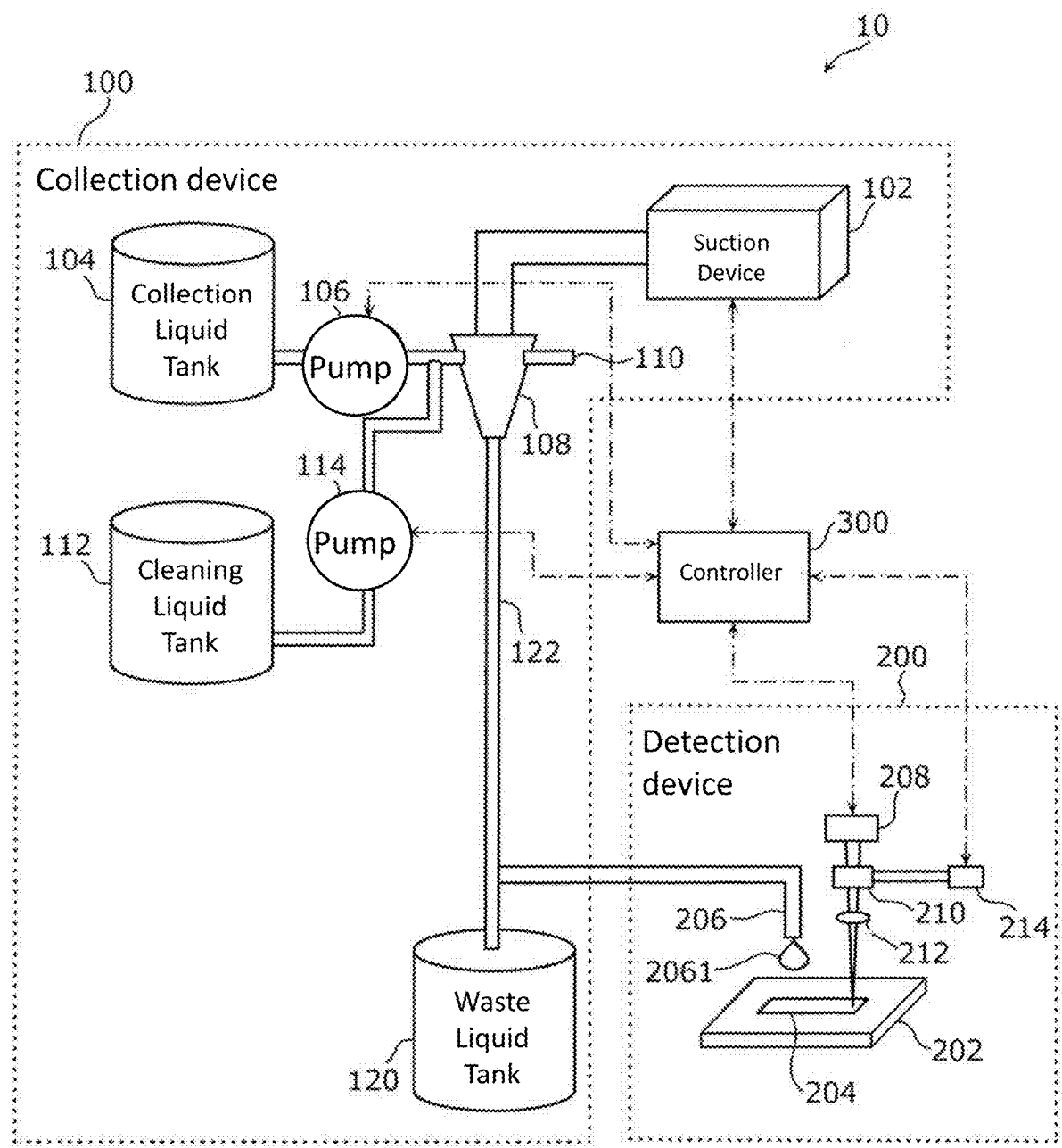
FIG. 1 is a schematic configuration diagram of a detection system according to an embodiment.

DETAILED DESCRIPTION OF THE EMBODIMENT (Findings Which Establish the Fundamental of the Present Disclosure)

As described above, the prior art described in Patent Literature 2 has an advantage that the enhanced electric field can be efficiently used by forming the organic molecular film that captures the target molecule on the hot site between the metal particles. In addition, since the gap between the adjacent metal particles is formed widely at the entrance side of the target molecule, there is an advantage that the enhanced electric field can be increased by narrowing the gap between the metal particles and that the probability that the target molecule is adsorbed to the organic molecular film can be increased. However, the degree of electric field enhancement is not necessarily sufficient, and it is difficult to detect a trace amount of an analyte.

In the prior art described in Patent Literature 3, the plurality of the metal fine protrusions are formed to be tapered along a height direction perpendicular to a principal surface of the substrate along a height direction perpendicular to a principal surface of the substrate, and the metal fine protrusions are connected by the flat part having the flat exposed surface. As a result, there is an advantage that the generation position and electric field intensity of plasmon resonance on the surface of the metal fine protrusion can be easily controlled. However, an electric field enhancement position and the electric field intensity on the surface of the metal fine protrusions are just controlled, and the electric field enhancement position and the electric field intensity in the whole of the plasmon resonance structure including the flat part are not controlled. As a result, the enhanced electric field fails to be used effectively.

The present inventors have intensively studied in view of the above problems. As a result, the inventors have arrived at a sensor substrate that can provide a large light emission enhancement. The present inventors have discovered that detection sensitivity of the detection device can be improved by using the sensor substrate for a detection device.

Therefore, the present disclosure provides a sensor substrate, a detection device, and a manufacturing method of the sensor substrate, with or by which a trace amount of an analyte is allowed to be detected.

The outline of one aspect of the present disclosure will be described below.

The sensor substrate according to one aspect of the present disclosure is a sensor substrate comprising:

a metal microstructure for generating surface plasmon when irradiated with excitation light, wherein the metal microstructure is composed of a plurality of protrusions disposed in a planar shape;

the plurality of the protrusions are disposed in such a manner that imaginary lines each passing through a center between adjacent protrusions draw a honeycomb shape in a plan view;

each of the plurality of the protrusions has a substantially hexagonal shape in a plan view; and a depth in a thickness direction of the sensor substrate of a gap present between the adjacent protrusions is larger than a radius of an imaginary circle inscribed in a hexagon forming the honeycomb shape.

According to this configuration, the plurality of the protrusions are disposed in such a manner that the imaginary lines each passing through the center between the adjacent protrusions draw a honeycomb shape in a plan view, and each of the plurality of the protrusions has a substantially hexagonal shape in a plan view. Thereby, since the width of a gap can be narrowed over the entire circumference of each of the plurality of the protrusions, an electric field enhancement effect can be improved. In addition, according to this configuration, the depth in the thickness direction of the sensor substrate of the gap present between the adjacent protrusions is larger than the radius of the imaginary circle inscribed in the hexagon forming the honeycomb shape. Thereby, since the depth of the gap can be also increased, the possibility of the analyte entering the gap can be increased. Therefore, if the sensor substrate according to one aspect of the present disclosure is used, the electric field enhancement effect can be improved, and a trace amount of an analyte can be detected.

In the sensor substrate according to one aspect of the present disclosure, it is preferable that the substantially hexagonal shape has an area of 80% or more of an area of the hexagon forming the honeycomb shape. In addition, it is preferable that the substantially hexagonal shape has an area of 98% or less of the area of the hexagon forming the honeycomb shape. According to this configuration, the width of the gap present between the plurality of the protrusions can be narrowed, the region where surface plasmon is generated is enlarged, and the electric field enhancement effect can be raised.

For example, in the sensor substrate according to one aspect of the present disclosure, a minimum width of the gap present between the adjacent protrusions may be more than 10 nm and less than 40 nm.

According to this configuration, the minimum width of the gap is more than 10 nm. As a result, it is possible to secure the width for the analyte entering the gap, and to further improve the possibility of the analyte that enters the gap. In addition, according to this configuration, the minimum width of the gap is less than 40 nm. Thereby, the electric field enhancement effect by the surface plasmon can be further improved.

For example, in the sensor substrate according to one aspect of the present disclosure, the depth of the gap in the thickness direction of the sensor substrate may be not less than 380 nm and not more than 510 nm.

Thereby, the possibility of the analyte entering the gap can be further increased, and a trace amount of the analyte can be detected with high sensitivity.

For example, in the sensor substrate according to one aspect of the present disclosure, the metal microstructure may include a resin substrate having a plurality of fine protrusions, and a metal film that is formed on the resin substrate and forms the plurality of the protrusions.

Thereby, the metal microstructure can be fabricated easily to reduce cost of the manufacture thereof.

For example, in the sensor substrate according to one aspect of the present disclosure, a bottom of the gap may be positioned below each top of the plurality of the fine protrusions.

Thus, since the gap is formed deeply, the possibility of the analyte entering the gap can be further increased.

For example, in the sensor substrate according to one aspect of the present disclosure, a thickness of the metal film is not less than 1.6 times and not more than 2.3 times as thick as a height of the plurality of the fine protrusions at the top of the plurality of the fine protrusions.

Thereby, for example, when the metal microstructure is formed by forming the metal film by sputtering, the gap can be adjusted to an appropriate width and depth.

For example, in the sensor substrate according to one aspect of the present disclosure, each of the plurality of the fine protrusions may be a cylinder having a diameter of not less than 140 nm and not more than 400 nm and a height of not less than 125 nm and not more than 225 nm, and the plurality of the fine protrusions may have a pitch of not less than 280 nm and not more than 520 nm.

Thereby, for example, a metal microstructure in which light having a wavelength of 750 nm to 850 nm, which is a wavelength having a small interaction with a substance contained in a virus, can be used as excitation light can be produced. Therefore, there is no autoluminescence by an antibody having a property of binding specifically to the analyte, and a trace amount of the analyte (here, a nucleoprotein of a virus) can be detected with high sensitivity.

For example, in the sensor substrate according to one aspect of the present disclosure, the thickness of the metal film may be not less than 310 nm and not more than 460 nm at the tops of the plurality of the fine protrusions.

Thereby, for example, in a case where the metal microstructure is produced by forming a metal film by sputtering, the gap can be adjusted to an appropriate width and depth.

In addition, a detection device according to one aspect of the present disclosure comprises:
  any one of the sensor substrates described above; wherein
  a first antibody having a property of binding specifically to an analyte is immobilized on the metal microstructure of the sensor substrate;
  the detection device further comprises:
  an introduction opening through which a second antibody and a sample pass to the metal microstructure; wherein the second antibody has a property of binding specifically to the analyte and is labeled with a fluorescent substance, and wherein the sample may include the analyte;
  a light irradiation part for irradiating the metal microstructure to which the second antibody and the sample has been introduced with the excitation light; and
  a detection part which detects the analyte based on fluorescence generated from the fluorescent substance by the irradiation with the excitation light.

Thereby, the analyte specifically captured by the first antibody can be detected with high sensitivity.

In addition, a manufacturing method of a sensor substrate according to one aspect of the present disclosure is a manufacturing method of a sensor substrate comprising a metal microstructure for generating surface plasmon when irradiated with excitation light, the method comprising:
  preparing a resin substrate having a plurality of fine protrusions; and
  forming a metal film on the resin substrate to form the sensor substrate comprising a metal microstructure having a plurality of protrusions,
  wherein
  the plurality of the protrusions are disposed in such a manner that imaginary lines each passing through a center between adjacent protrusions draw a honeycomb shape in a plan view;
  each of the plurality of the protrusions has a substantially hexagonal shape in a plan view, and
  a depth in a thickness direction of the sensor substrate of a gap present between the adjacent protrusions is larger than a radius of an imaginary circle inscribed in a hexagon forming the honeycomb shape.

Thereby, a sensor substrate having the above-described metal microstructure can be manufactured.

Hereinafter, an embodiment will be specifically described with reference to the drawings.

It should be noted that the embodiment which will be described below shows a comprehensive or specific example. The numerical values, shapes, materials, constituent elements, arrangement positions and connection forms of the constituent elements, processes, the order of the processes, and the like which will be shown in the following embodiment are merely examples, and are not intended to limit the scope of the claims. In addition, among the constituent elements in the following embodiments, constituent elements that are not described in the independent claims indicating the highest concept will be described as optional constituent elements.

Also, the drawings are not necessarily shown accurately. In each drawing, substantially the same configuration is denoted by the same reference numeral, and redundant description is omitted or simplified.

In the following embodiment, a case where the analyte is a component constituting a virus that floats in the air (hereinafter, simply referred to as a virus) will be described. However, in the present disclosure, the analyte is not limited to this. The component constituting the virus is, for example, a protein constituting the virus or a nucleic acid. The type of the virus is not particularly limited, and any virus can be used as long as it is generally classified as a virus. Further, the analyte does not have to be a virus.

Embodiment

[Outline of Detection System]

FIG. 1 is a schematic configuration diagram of a detection system 10 according to the embodiment. The detection system 10 is provided, for example, in a room which people enter and exit. As shown in FIG. 1, the detection system 10 comprises a collection device 100, a detection device 200, and a controller 300. Hereinafter, the details of the collection device 100, the detection device 200, and the controller 300 will be described.

[Configuration of Collection Device]

The collection device 100 collects fine particles that may contain a virus in the air to mixes the fine particles with a collection liquid. As shown in FIG. 1, the collection device 100 comprise a suction device 102, a collection liquid tank 104, a pump 106, a cyclone 108, an air suction opening 110, a cleaning liquid tank 112, a pump 114, and a waste liquid tank 120, and a liquid channel 122. Hereinafter, each constituent element of the collection device 100 will be described.

The suction device 102 sucks ambient atmospheric air from the air suction opening 110. Fine particles that may contain a virus floating in the ambient atmospheric air are sucked into the cyclone 108 from the air suction opening 110 together with the air.

The pump 106 supplies the collection liquid in the collection liquid tank 104 to the cyclone 108.

The cyclone 108 is connected to the air suction opening 110 and the collection liquid tank 104, and mixes the fine particles that may contain the virus in the air sucked from the air suction opening 110 by the suction device 102 with the collection liquid supplied from the collection liquid tank 104 by the pump 106. The cyclone 108 is connected to the detection device 200 through the liquid channel 122. The collection liquid mixed with the fine particles (hereinafter, referred to as a sample) is discharged from the cyclone 108 to the detection device 200 through the liquid channel 122.

The cleaning liquid tank 112 is a container for holding a cleaning liquid for cleaning the cyclone 108 and the liquid channel 122. The cleaning liquid tank 112 is connected to the cyclone 108. The cleaning liquid in the cleaning liquid tank 112 is supplied to the cyclone 108 by the pump 114.

The waste liquid tank 120 is a container for storing unnecessary liquid.

The liquid channel 122 is a path for guiding the sample output from the cyclone 108 to the detection device 200.

[Configuration of Detection Device]

Figure 2:
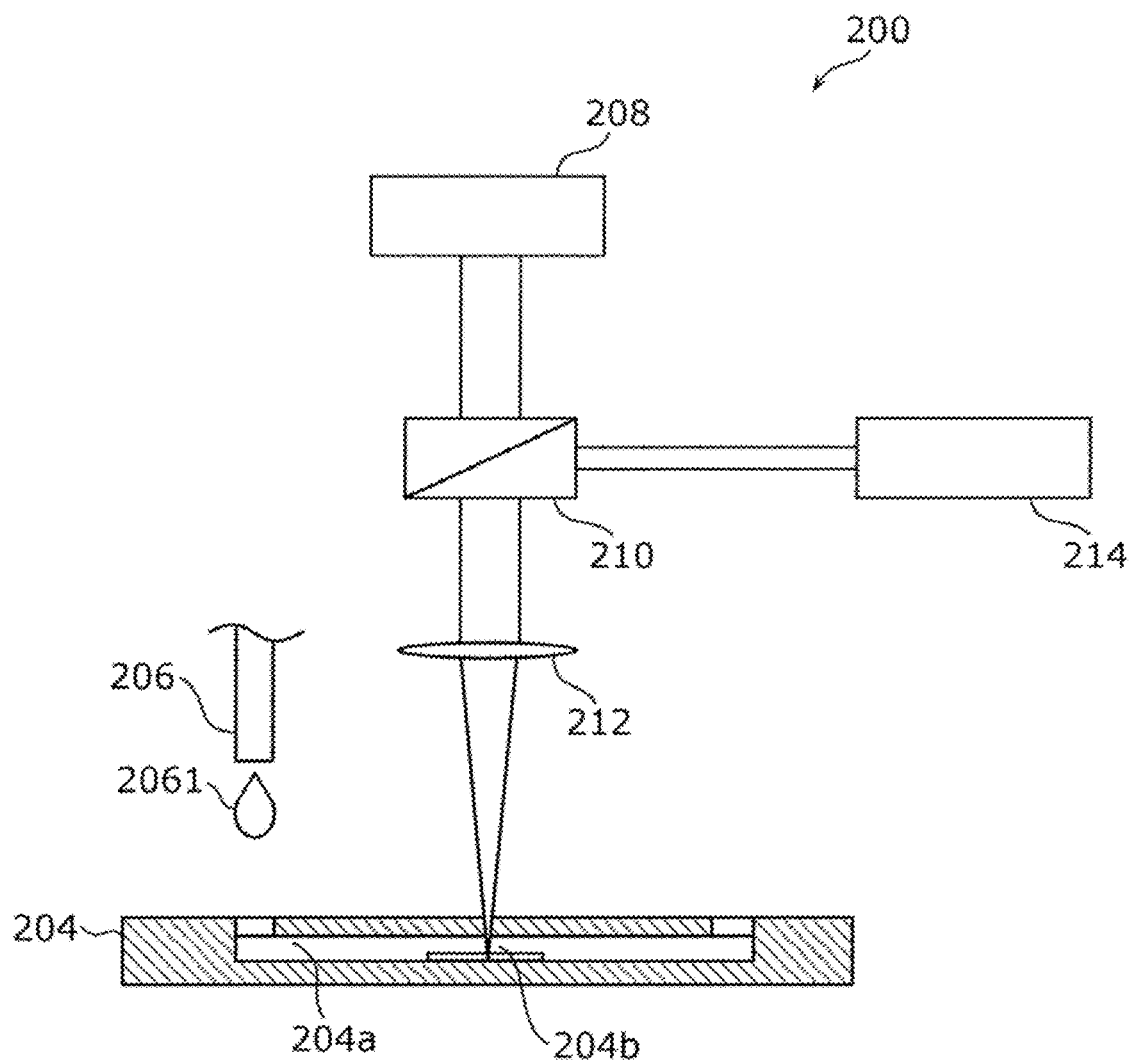
FIG. 2 is a schematic configuration diagram of a detection device according to the embodiment.
Figure 3:
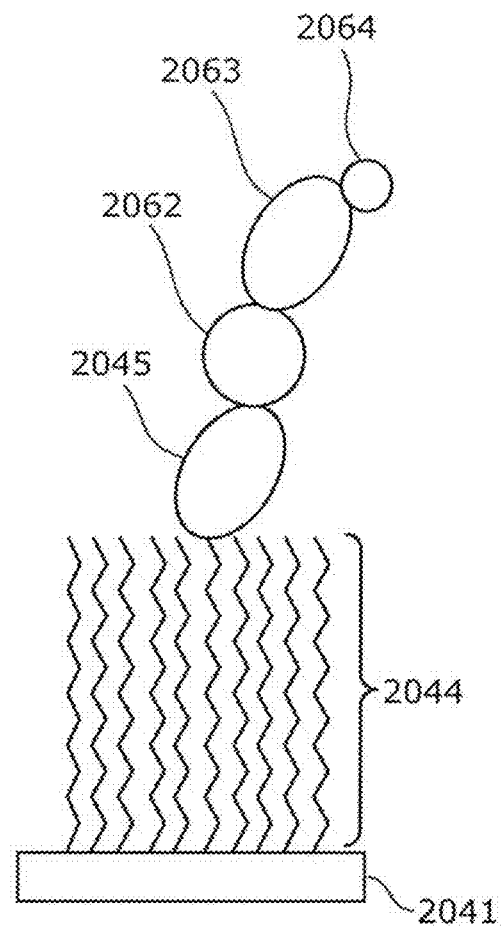
FIG. 3 is a diagram showing a SAM on a metal microstructure on a sensor substrate according to the embodiment.

Next, the detection device 200 will be specifically described with reference to FIGS. 1, 2, and 3. FIG. 2 is a configuration diagram of the detection device 200 according to the embodiment. FIG. 3 is a diagram showing a SAM (i.e., Self-Assembled Monolayer) 2044 on the metal microstructure on a sensor substrate 204b according to the embodiment.

The detection device 200 detects a virus from the collection liquid in which the fine particles have been mixed by the collection device 100. As shown in FIGS. 1 and 2, the detection device 200 comprises a sensor device 202, an introduction opening 206, a light source 208, a beam splitter 210, a lens 212, and a detection part 214. Hereinafter, each constituent element of the detection device 200 will be described.

The sensor device 202 comprises a sensor cell 204. The sensor device 202 comprises one sensor cell 204; however, the sensor device 202 may comprise a plurality of sensor cells 204.

In the present embodiment, the sensor device 202 can detect a virus in the concentration range of 0.1 pM to 100 nM. In the present embodiment, a surface-enhanced fluorescence method is used to optically detect an amount of the virus.

The sensor cell 204 enhances fluorescence from a fluorescent substance bound to the virus by generating surface plasmon when irradiated with excitation light. As shown in FIG. 2, the sensor cell 204 is disposed in the sensor device 202 and comprises a flow path 204a and the sensor substrate 204b.

The flow path 204a is a path for guiding a sample liquid 2061 dropped from the introduction opening 206 to the sensor substrate 204b.

The sensor substrate 204b is an region for optically detecting the virus using surface plasmon. A metal microstructure is disposed on the sensor substrate 204b, and the surface plasmon is generated when the light source 208 is irradiated with excitation light. In addition, as shown in FIG. 3, a first VHH antibody 2045 is immobilized on the metal microstructure of the sensor substrate 204b. The first VHH antibody 2045 is an immobilized antibody capable of binding specifically to the virus. Details of the sensor substrate 204b will be described later with reference to FIGS. 4A and 4B.

The second antibody and the sample are introduced into the sensor cell 204 through the introduction part 206. The sample liquid 2061 containing the second VHH antibody 2063 and the sample is dropped onto the sensor cell 204 through the introduction part 206. The second VHH antibody 2063 is a labeled antibody labeled with a fluorescent substance 2064. The sample is a liquid that may contain a virus 2062, and in the present embodiment, the sample is a collection liquid discharged from the cyclone 108.

If the virus 2062 is included in the sample, the virus 2062 binds to the metal microstructure of the sensor substrate 204b through the first VHH antibody 2045. At this time, the virus 2062 is also bound to the second VHH antibody 2063 labeled with the fluorescent substance 2064. In other words, a composite of the first VHH antibody 2045, the virus 2062, the second VHH antibody 2063, and the fluorescent substance 2064 is bonded to the metal microstructure of the sensor substrate 204b. In this state, by irradiating the metal microstructure of the sensor substrate 204b with light, fluorescence is emitted from the fluorescent substance 2064 bonded indirectly to the virus 2062, and the fluorescence is enhanced by surface plasmon. Hereinafter, the fluorescence enhanced by the surface plasmon is referred to as surface-enhanced fluorescence. The first antibody and the second antibody will be described using a VHH antibody as an example. However, the first antibody and the second antibody are not limited to the VHH antibody, and may be an IgG antibody.

In FIG. 3, a SAM 2044 is formed on the metal microstructure of the sensor substrate 204b. In the present embodiment, the SAM 2044 includes, for example, an alkyl chain having about 6 carbon atoms. The first VHH antibody 2045 is immobilized on the metal microstructure of the sensor substrate 204b through the SAM 2044.

When the virus (analyte) 2062 is contained in the sample liquid 2061, the virus 2062 binds to the first VHH antibody 2045 immobilized on the metal microstructure of the sensor substrate 204b. The second VHH antibody 2063 labeled with the fluorescent substance 2064 has been also bound to the virus 2062.

By irradiating such a metal microstructure with excitation light, fluorescence is emitted from the fluorescent substance 2064, and the fluorescence is enhanced by surface plasmon generated on the metal microstructure of the sensor substrate 204b. In other words, the surface-enhanced fluorescence, depending on the amount of the virus 2062 is emitted.

The light source 208 is one example of a light irradiation part for irradiating the sensor cell 204 with excitation light. As the light source 208, a known technique can be used without any particular limitation. For example, a laser such as a semiconductor laser or a gas laser can be used as the light source 208. It is preferable that the light source 208 emits excitation light having a wavelength that has a small interaction with a substance contained in the virus (for example, 400 nm to 2000 nm). Furthermore, it is preferable that the wavelength of the excitation light is 600 nm to 850 nm, which can be used by the semiconductor laser. In the present embodiment, the wavelength of the excitation light and the wavelength emitted by the fluorescent substance are 750 nm to 850 nm.

The beam splitter 210 separates the surface-enhanced fluorescence generated on the sensor substrate 204b from the excitation light emitted from the light source 208. Specifically, the excitation light from the light source 208 passes through the beam splitter 210, and the beam splitter 210 separates the surface-enhanced fluorescence generated on the sensor cell 204 to guide the separated surface-enhanced fluorescence to the detection part 214.

The lens 212 condenses the excitation light from the light source 208 that has passed through the beam splitter 210 onto the sensor substrate 204b.

The detection part 214 splits the surface-enhanced fluorescence guided by the beam splitter 210 and detects light within a specific wavelength region, to output an electrical signal corresponding to the amount of the virus in the sample. As long as the detection part 214 can detect the light of the specific wavelength, a known technique can be used without any particular limitation. For example, as the detection part 214, an interference filter through which a specific wavelength of light can pass, a Zellny spectroscope for splitting light using a diffraction lattice, an echelle spectroscope, or the like can be used. Furthermore, the detection part 214 may include a notch filter for removing excitation light from the light source 208, or a long pass filter capable of blocking the excitation light from the light source 208 and passing the surface-enhanced fluorescence generated in the sensor cell 204.

[Configuration of Controller]

As shown in FIG. 1, the controller 300 controls the operation of the entire detection system 10. Specifically, the controller 300 controls the collection device 100 and the detection device 200.

More specifically, the controller 300 controls the start of measurement, causes the suction device 102 to start sucking ambient air, and causes the pump 106 to supply the collection liquid from the collection liquid tank 104 to the cyclone 108. As a result, the collection liquid and the fine particles are mixed with each other in the cyclone 108, and the sample is supplied from the cyclone 108 to the detection device 200. Furthermore, the controller 300 causes the light source 208 to emit light and causes the detection part 214 to detect surface-enhanced fluorescence.

For example, the controller 300 can supply a predetermined volume of the sample liquid 2061 to the detection device 200 by controlling each pump under a preset condition based on the input parameter. Further, the controller 300 may have a time measuring function, and the controller 300 may generate and store information on the time required for each operation. In addition, the controller 300 may receive a measurement value from the detection device 200 and calculate a temporal change in the concentration of the virus floating in the air based on the measurement value and the information on the time.

The controller 300 is realized by, for example, one or more dedicated electronic circuit. The one or more dedicated electronic circuit may be integrated on one chip, or may be individually formed on a plurality of chips. The controller 300 may be realized by a general-purpose processor (not shown) and a memory (not shown) in which a software program or an instruction has been stored, in place of the one or more dedicated electronic circuit. In this case, the processor functions as the controller 300, when the software program or the instruction is executed.

[Configuration of Sensor Substrate]

Here, the detailed configuration of the sensor substrate 204b will be specifically described with reference to FIGS. 4A, 4B, and 5.

Figure 4A:
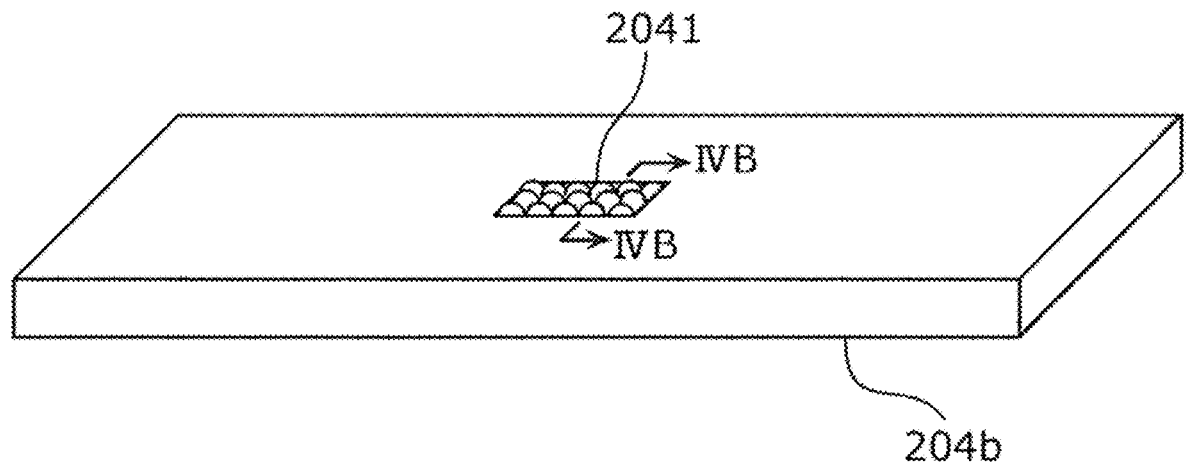
FIG. 4A is a perspective view of the sensor substrate according to the embodiment.

FIG. 4A is a perspective view of the sensor substrate 204b of the sensor cell 204 in the embodiment. FIG. 4B is an enlarged cross-sectional view of a metal microstructure 2041 taken along the line IVB-IVB in FIG. 4A.

As shown in FIG. 4A, the sensor substrate 204b is provided with the nanoscale metal microstructure 2041 for generating plasmon resonance. In the present embodiment, as shown in FIG. 4B, the metal microstructure 2041 comprises a resin substrate 2042 and a metal film 2043.

The resin substrate 2042 has a plurality of fine protrusions 2042a formed by nanoimprinting or injection molding. Here, an example in which the plurality of the fine protrusions 2042a have a pillar shape (cylindrical shape) is shown. In the plurality of the fine protrusions 2042a, a ratio between the height H of the fine protrusions and the size of the pitch P between the fine protrusions 2042a is preferably 1:1 to 1:3.

In the present embodiment, the wavelength of the excitation light and the wavelength of fluorescence are, for example, wavelengths within the range of 750 nm to 850 nm, which are wavelengths each having a small interaction with a substance contained in the virus. Therefore, in the present embodiment, for example, it is preferable that the plurality of the fine protrusions 2042a are cylinders each having a diameter D of not less than 140 nm and not more than 400 nm and a height H of not less than 125 nm and not more than 225 nm, and that the pitch P between the fine protrusions 2042a is not less than 280 nm and not more than 520 nm. In particular, it is preferable that the plurality of the fine protrusions 2042a are cylinders each having a diameter D of about 230 nm and a height H of about 200 nm, and that the pitch between the fine protrusions 2043a is about 460 nm. The plurality of the fine protrusions 2042a of the resin substrate 2042 is not limited to this, and may include a plurality of hemispheres in place of the plurality of cylinders.

Figure 4B:
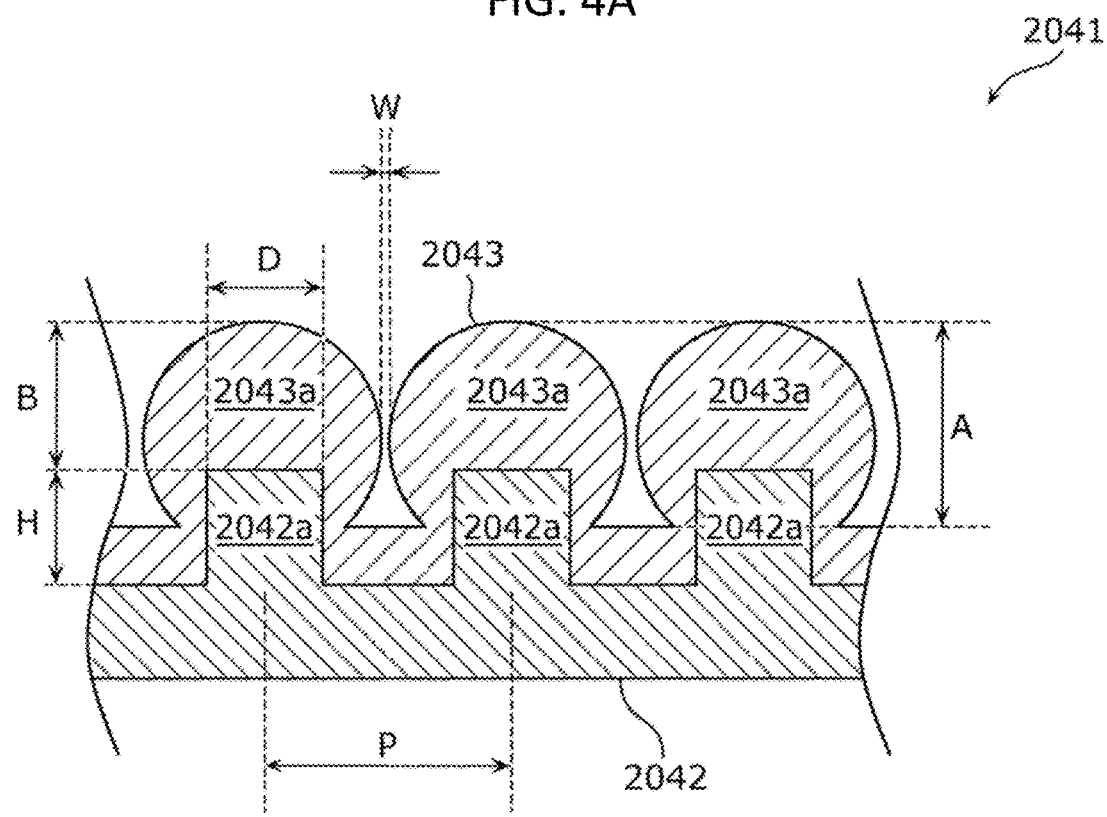
FIG. 4B is an enlarged cross-sectional view taken along the line IVB-IVB in FIG. 4A.

As shown in FIG. 4B, the metal film 2043 is formed by forming a metal film on the resin substrate 2042. The SAM 2044 is formed on the metal film 2043, and the first VHH antibody 2045 is immobilized above the metal microstructure 2041 through the SAM 2044. In the metal film 2043, a plurality of protrusions 2043a corresponding to the plurality of the fine protrusions 2042a of the resin substrate 2042 are formed. In a case where the wavelength of the excitation light and the wavelength of the fluorescence are 750 nm to 850 nm, it is preferable that the thickness B of the metal film 2043 is not less than 1.6 times and not more than 2.3 times as thick as the height H of the plurality of the fine protrusions at the top of the plurality of the fine protrusions. At this time, it is preferable that the thickness B of the metal film 2043 is preferably not less than 310 nm and not more than 460 nm at the top of the plurality of the fine protrusions. In particular, the thickness B of the metal film 2043 is preferably about 385 nm. In addition, the minimum width W of the gap between adjacent protrusions in the plurality of the protrusions 2043a may be greater than 10 nm and less than 40 nm. The depth A of the gap in the thickness direction of the sensor substrate is preferably not less than 380 nm and not more than 510 nm. It is preferable that the bottom of the gap is positioned below each top of the plurality of the fine protrusions.

The material of the metal film 2043 is not particularly limited, and may be gold, silver, copper, aluminum, or an alloy containing these metals as a main component. In the present embodiment, a method for forming the metal film 2043 is not particularly limited, and may be formed by sputtering or vacuum deposition, for example.

Referring to FIGS. 4A and 4B again, the sensor substrate 204b according to the present embodiment comprises the metal microstructure 2041. The metal microstructure 2041 generates surface plasmon when irradiated with excitation light. The metal microstructure 2041 is composed of the plurality of the protrusions 2043a disposed in a planar shape.

Next, the metal microstructure 2041 provided in the sensor substrate 204b according to the present embodiment will be specifically described with reference to FIG. 5. FIG. 5 is a diagram illustrating the metal microstructure 2041 provided in the sensor substrate 204b according to the embodiment.

Figure 5:
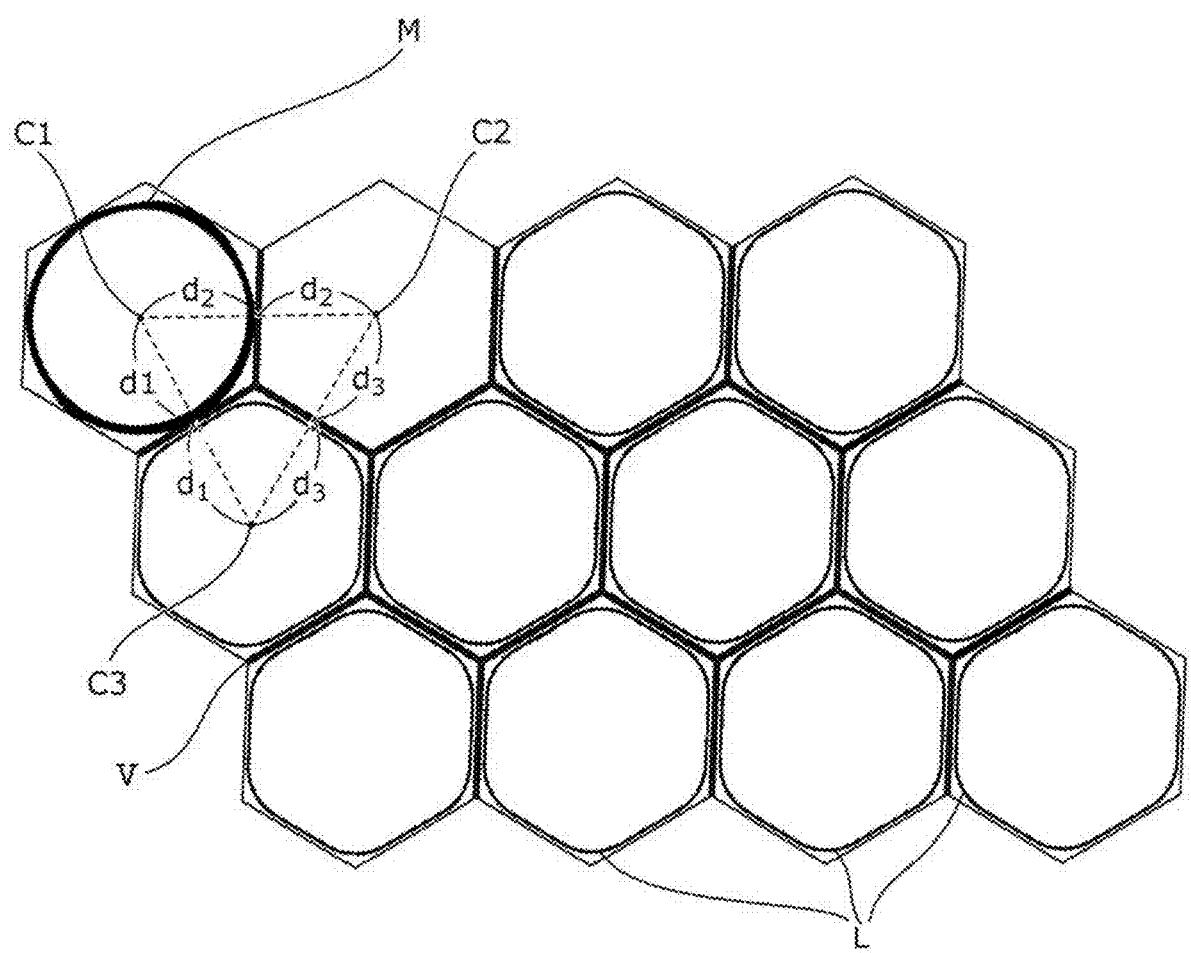
FIG. 5 is a diagram illustrating the metal microstructure in the embodiment.

In FIG. 5, the outline L is a contour in a plan view of the plurality of the protrusions 2043a (see FIG. 4B). The plurality of the protrusions 2043a are disposed such that imaginary lines V each passing through the center between adjacent protrusions 2043a draw a honeycomb shape. For example, the centers of the three protrusions 2043a adjacent to one another are defined as C1, C2, and C3. One center between the two adjacent protrusions 2043a is positioned at a midpoint at which a line segment connecting the centers C1 and C3 is divided equally into d1. Similarly, another center between the two protrusions 2043a in contact with each other is located at a midpoint at which a line segment connecting the centers C1 and C2 is divided equally into d2. Still another center between the two protrusions 2043a in contact with each other is located at a midpoint at which a line segment connecting the centers C2 and C3 is divided equally into d3. Imaginary lines V each passing through the center between the adjacent protrusions 2043a draw a honeycomb shape, in a case where a perpendicular bisector of a line segment which connects centers of the adjacent protrusions 2043a is connected to a perpendicular bisector of another line segment. In addition, the shape of the outline L, namely, the shape of each of the plurality of the protrusions 2043a is substantially a hexagonal shape in a plan view. In addition, in FIG. 5, the imaginary circle M is inscribed in the hexagon which forms the honeycomb shape.

The substantially hexagonal shape may be, for example, a complete hexagonal shape, a hexagonal shape with rounded corners, or a shape composed of lines each having a slight curvature on each side of the hexagon.

Next, a merit provided by that each of the plurality of the protrusions 2043a has a substantially hexagonal shape will be described. In general, it is known that the electric field enhancement by plasmon is large in a small gap (nano gap) formed between metals. In a case where the shape of each of the plurality of the protrusions is a spherical shape, the region having the minimum width of the gap between the adjacent protrusions exists as a point in a plan view. On the other hand, as disclosed in the present disclosure, in a case where the shape of each of the plurality of the protrusions 2043a is substantially hexagonal in a plan view, the region of the minimum width W of the gap between the adjacent protrusions 2043a (see FIG. 4B) forms a line, since the region exists over the entire circumference of each of the protrusions 2043a. In other words, in a case where the shape of each of the plurality of the protrusions 2043a is a substantially hexagonal shape in a plan view, the area of the region of the minimum width W of the gap per unit area increases. As a result, the electric field enhancement effect is greater in the case than in a case where the shape of the plurality of the protrusions is a spherical shape.

In other words, since the width of the gap can be narrowed over substantially the entire circumference of each of the plurality of the protrusions 2043a, the region where the surface plasmon is generated is enlarged, and the electric field enhancement effect can be raised.

Conventionally, Au film over nanosphere (AuFON) is known in which polystyrene spheres and the like are arranged on a substrate so as to have a microstructure, and a metal film (Au) is formed thereon to form a plurality of protrusions. In addition, a structure has been reported in which a plurality of protrusions forming a metal microstructure are in a shape close to a hexagonal shape in a plan view. However, these metal microstructures have limited light emission enhancement, since the nanogap between the plurality of the protrusions is formed shallowly in a cross-sectional view. As another problem, since it is significantly different to produce AuFON stably, AuFON is used for research; however it is significantly difficult to use AuFON for products from the viewpoint of productivity and reproducibility.

On the other hand, although not shown in FIG. 5, the depth A in the thickness direction of the sensor substrate 204b of the gap between the adjacent protrusions 2043a (see FIG. 4B) is larger than the radius of the imaginary circle. Thereby, since the depth of the gap can be formed deeply, the possibility of the analyte that enters the gap can be increased. Further, since the surface plasmon is maximized in the gap, as the depth of the gap is increased, the region where the surface plasmon is generated is larger in the depth direction, and the electric field enhancement effect can be enhanced.

[Manufacturing Method of Sensor Substrate]

Figure 6:
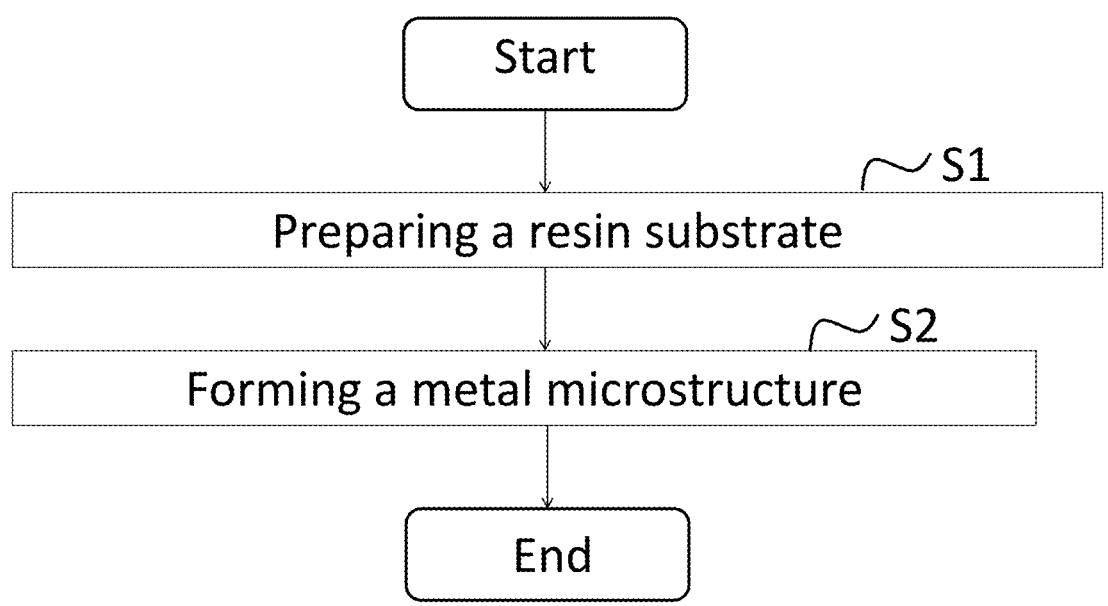
FIG. 6 is a flowchart illustrating a manufacturing method of the sensor substrate according to the embodiment.

Subsequently, a manufacturing method of the sensor substrate according to the present embodiment will be specifically described with reference to FIG. 6. FIG. 6 is a flowchart illustrating a manufacturing method of the sensor substrate according to the present embodiment.

As shown in FIG. 6, the manufacturing method of the sensor substrate according to the present embodiment includes a step S1 of preparing a resin substrate having a plurality of fine protrusions, and a step S2 of forming a metal film on the resin substrate to form the sensor substrate comprising a metal microstructure having a plurality of protrusions.

In the step S1 of preparing the resin substrate, a forming method is not particularly limited, as long as the plurality of the fine protrusions is formed on the resin substrate. For example, a nanoimprint method or an injection molding method may be used. The shape of each of the fine protrusions may be a pillar shape (a cylindrical shape) or a hemispherical shape. In a case where the shape of each of the plurality of the fine protrusions is a cylindrical shape, each of the plurality of the fine protrusions may be formed with the diameter, the height, and the pitch, all of which have been described above.

In the step S2 of forming the sensor substrate, a metal film is formed on the resin substrate having the plurality of the fine protrusions provided in the step S1 of preparing the resin substrate. In this way, the metal microstructure having the plurality of the protrusions is formed to provide the sensor substrate having the metal microstructure. The region where the metal microstructure has been formed is referred to as a detection region. Examples of the method for forming the metal film are a sputtering method and a vacuum deposition method. The metal film is formed only in the detection region where the plurality of the fine protrusions have been formed on the resin substrate. The sensor substrate according to the present embodiment is one example, and may be formed in a desired size and shape.

In the above manufacturing method, a manufacturing method of the sensor substrate comprising the metal microstructure having the plurality of the protrusions by forming the metal film on the resin substrate having the plurality of the fine protrusions has been described. The sensor substrate may be manufactured by forming the metal microstructure and then incorporating the metal microstructure into another substrate.

EXAMPLES

Hereinafter, the present disclosure will be described in more detail with reference to experimental examples; however, these experimental examples do not limit the present disclosure in any way.

[Production of Sensor Substrate]

As a resin substrate having a plurality of fine protrusions, a resin substrate having a plurality of pillar-shaped fine protrusions formed by nanoimprinting was used. Each of the plurality of the fine protrusions had a height of 200 nm, a diameter of 230 nm, and two adjacent fine protrusions had a pitch of 460 nm. Subsequently, the resin substrate was load into a sputtering device and evacuated to a predetermined value ($2 \times 10^{-4}$ Pa to $8 \times 10^{-4}$ Pa). Then, gold (Au) was formed on each of the resin substrates by sputtering such that thicknesses from the top of the fine protrusion (hereinafter, referred to as the protrusion Au film thickness) were 190 nm, 290 nm, 385 nm, 435 nm, and 480 nm. Thus, a sensor substrate having a metal microstructure was produced. Sputtering was appropriately adjusted within the following conditions.

Output: 20 W to 30 W
Time: 1000 seconds to 2000 seconds
Argon gas flow rate: 10 sccm to 30 sccm
Substrate rotation speed: 10 rpm to 30 rpm
Distance between target and substrate: 80 mm to 120 mm The metal microstructure of the provided sensor substrate was observed with a scanning electron microscope (SEM).

FIG. 7A to FIG. 7E are plane SEM images of the metal microstructures in which the protrusion Au film thicknesses were 190 nm (Experimental Example A), 290 nm (Experimental Example B), 385 nm (Experimental Example C), 435 nm (Experimental Example D), and 480 nm (Experimental Example E), respectively. Experimental Examples C and D correspond to Inventive Examples in the present disclosure, and Experimental Examples A, B, and E correspond to Comparative Examples.

Figure 7A:
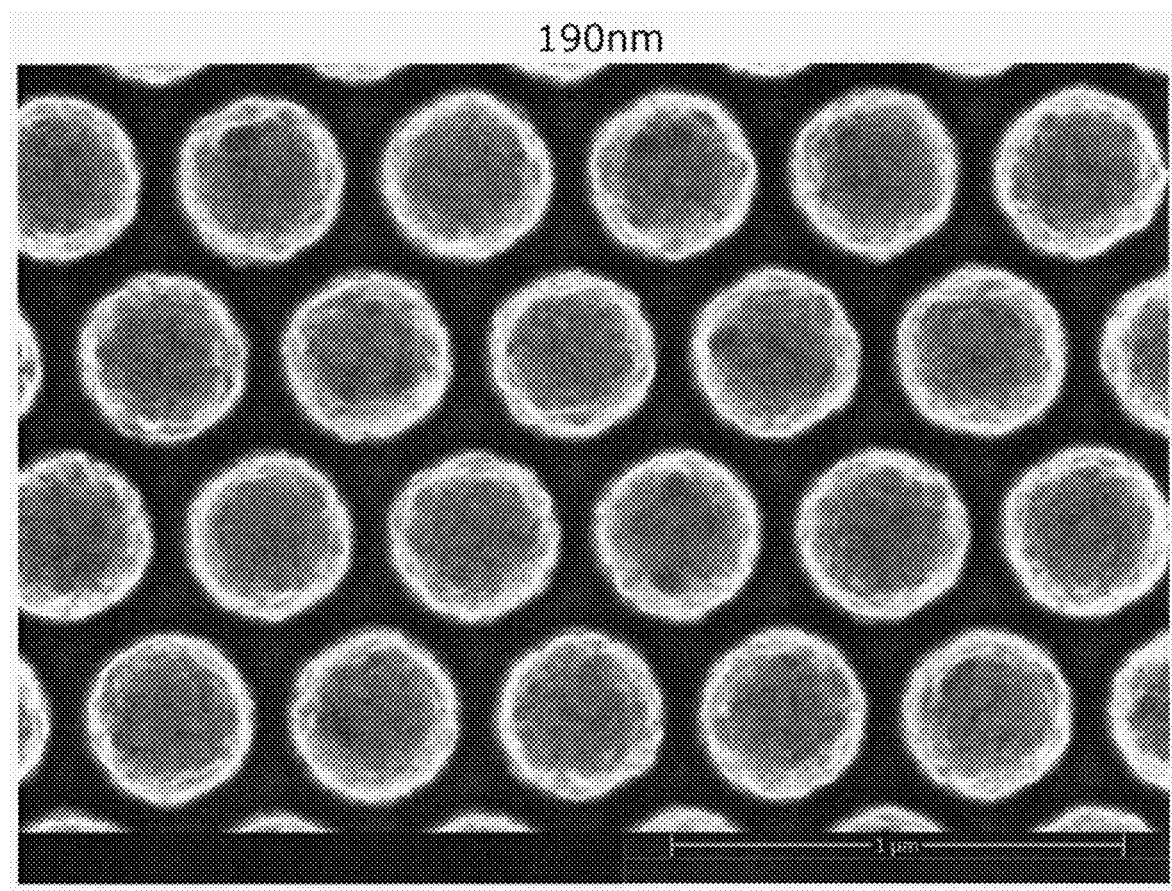
FIG. 7A is a diagram showing a planar SEM image of a metal microstructure of Experimental Example A.

As shown in FIG. 7A, in Experimental Example A, since the metal film is relatively thin, the metal film is formed in accordance with the shape of the plurality of the fine protrusions. Therefore, the shape of each of the plurality of the protrusions forming the metal microstructure is a circular shape in a plan view.

As shown in FIGS. 7B to 7E, the shape of the plurality of the protrusions starts to change gradually as the film thickness increases from the vicinity of the protrusion Au film thickness of 290 nm (Experimental Example B). In other words, the shape of each of the plurality of the protrusions forming the metal microstructure starts to change from the circular shape to a hexagonal shape in a plan view. In Experimental Example E shown in FIG. 7E, the shape of each of the plurality of the protrusions forming the metal microstructure is significantly close to a hexagon.

Figure 7B:
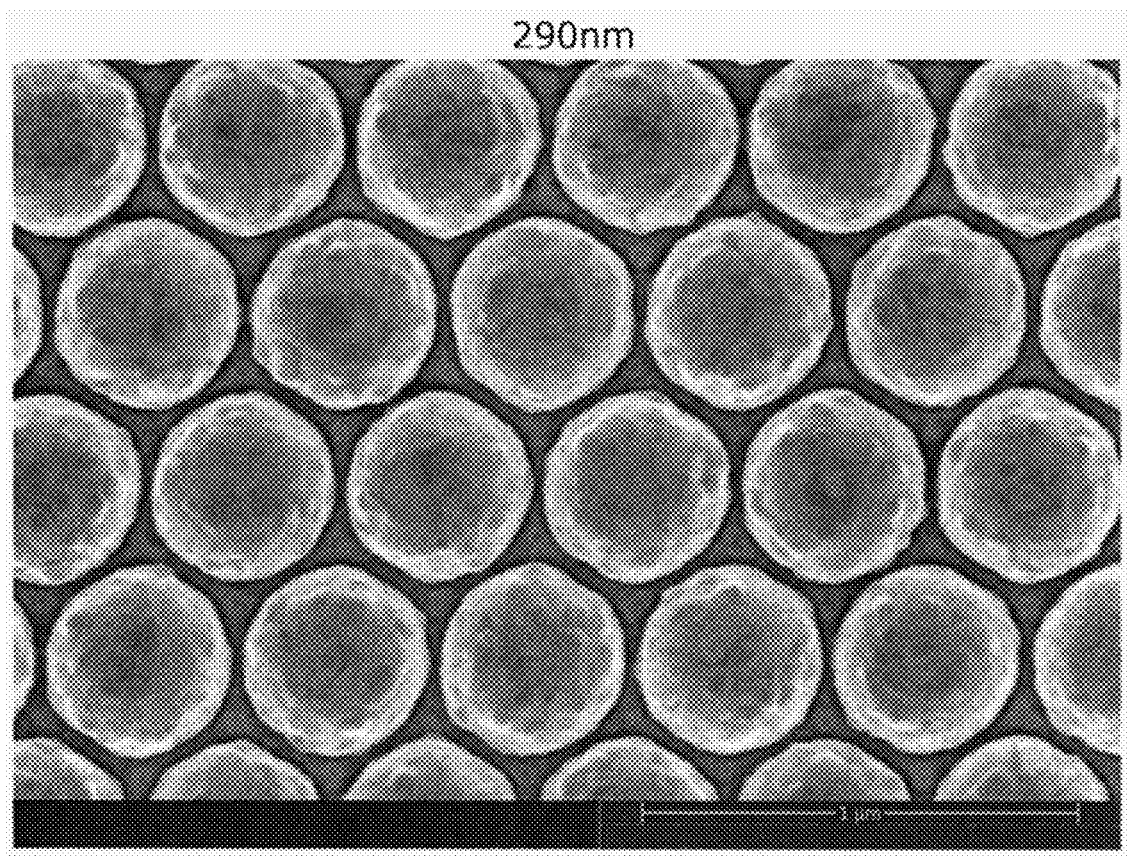
FIG. 7B is a diagram showing a planar SEM image of a metal microstructure of Experimental Example B.

Here, in the metal microstructure of Experimental Example B shown in FIG. 7B, each of the plurality of the protrusions has a circular shape in a plan view.

Figure 7C:
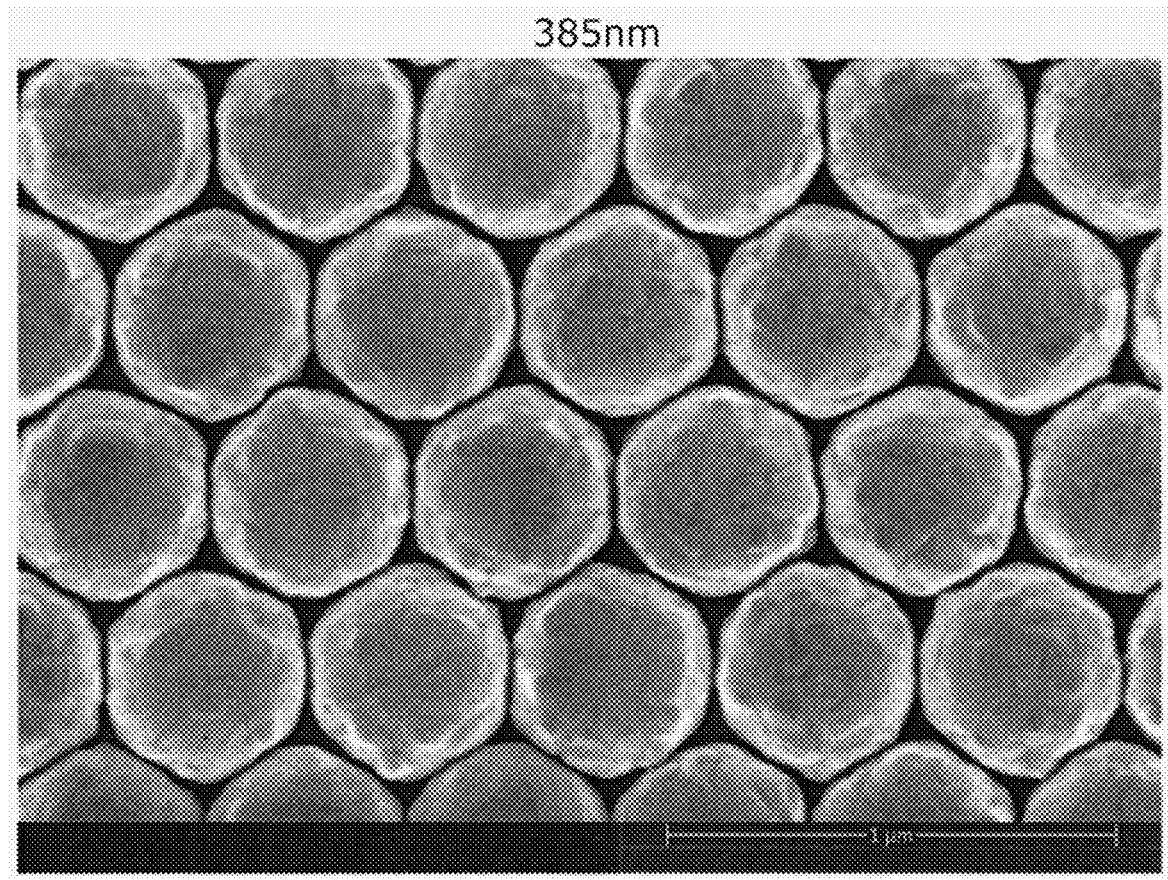
FIG. 7C is a diagram showing a planar SEM image of a metal microstructure of Experimental Example C.
Figure 7D:
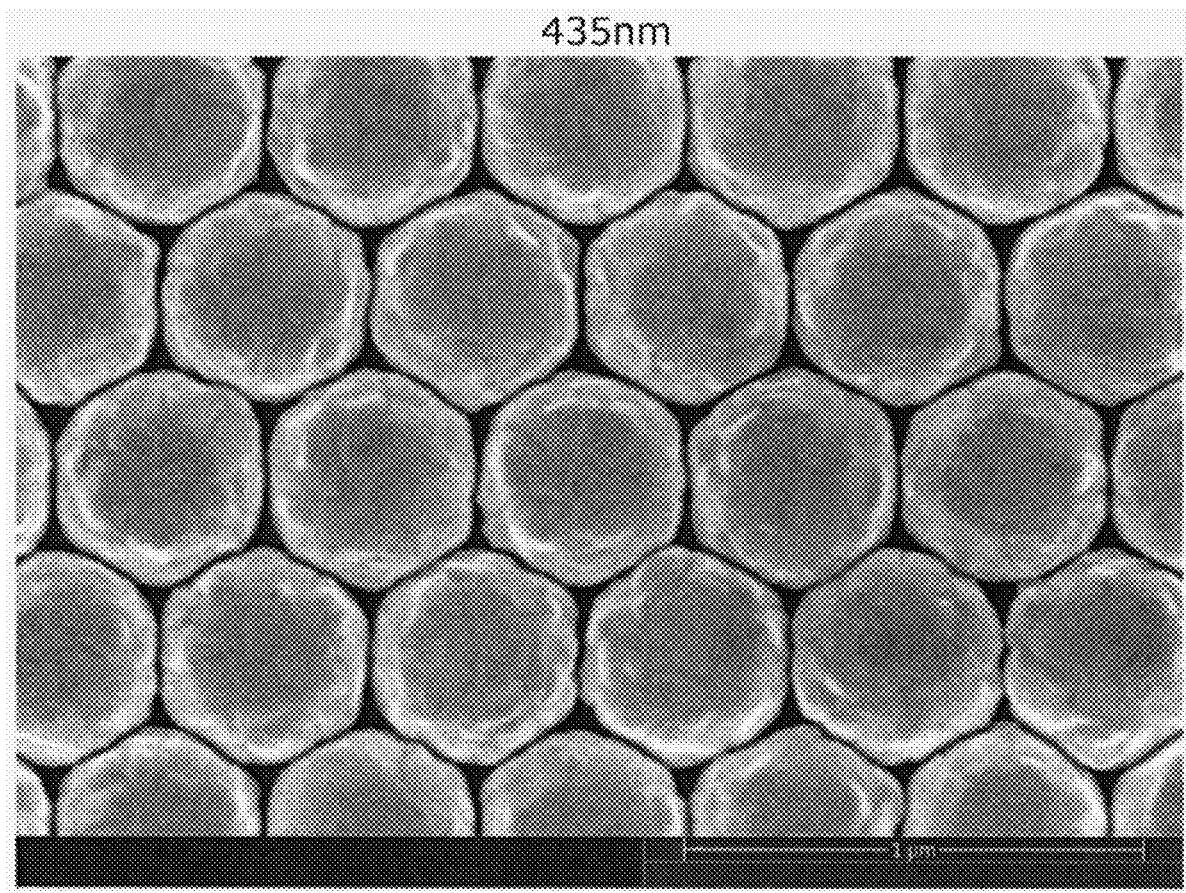
FIG. 7D is a diagram showing a planar SEM image of a metal microstructure of Experimental Example D.
Figure 7E:
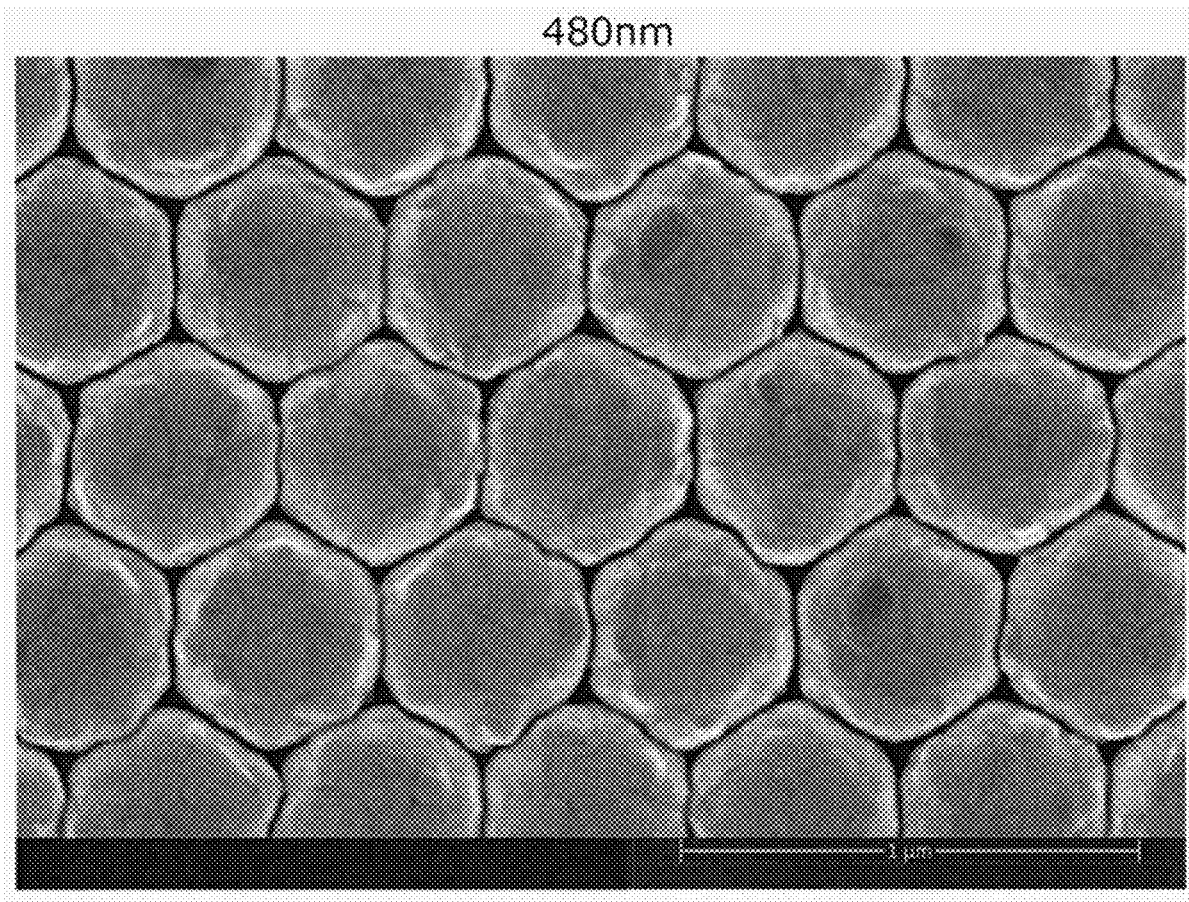
FIG. 7E is a diagram showing a planar SEM image of a metal microstructure of Experimental Example E.

On the other hand, in the metal microstructures of Experimental Examples C to E shown in FIGS. 7C to 7E, each of the plurality of the protrusions has a substantially hexagonal shape in a plan view.

Hereinafter, the reason why each of the plurality of the protrusions approaches the hexagonal shape will be described. Normally, when a metal film is formed on a plurality of fine protrusions each having a cylindrical shape, the metal film grows in such a way that each of the plurality of the protrusions has a spherical shape (a circular shape in a plan view with respect to the sensor substrate). As the forming of the film is continued to increase the thickness of the metal film, the gap between the adjacent protrusions is narrowed. When the gap between the adjacent protrusions is narrowed, the formation of the film on lateral surfaces of each of the adjacent protrusions is suppressed in the narrowed gap. On the other hand, in a part where the gap between adjacent protrusions is wide, for example, a gap surrounded by three protrusions adjacent to one another, the formation of the film on the lateral surfaces of each of the adjacent protrusions is less likely to be suppressed. Therefore, as a result, as disclosed in the present disclosure, the shape of each of the plurality of the protrusions forming the metal microstructure is a substantially hexagonal shape in a plan view.

FIGS. 8A to 8E are perspective SEM images of the metal microstructures of Experimental Examples A to E, respectively.

Figure 8A:
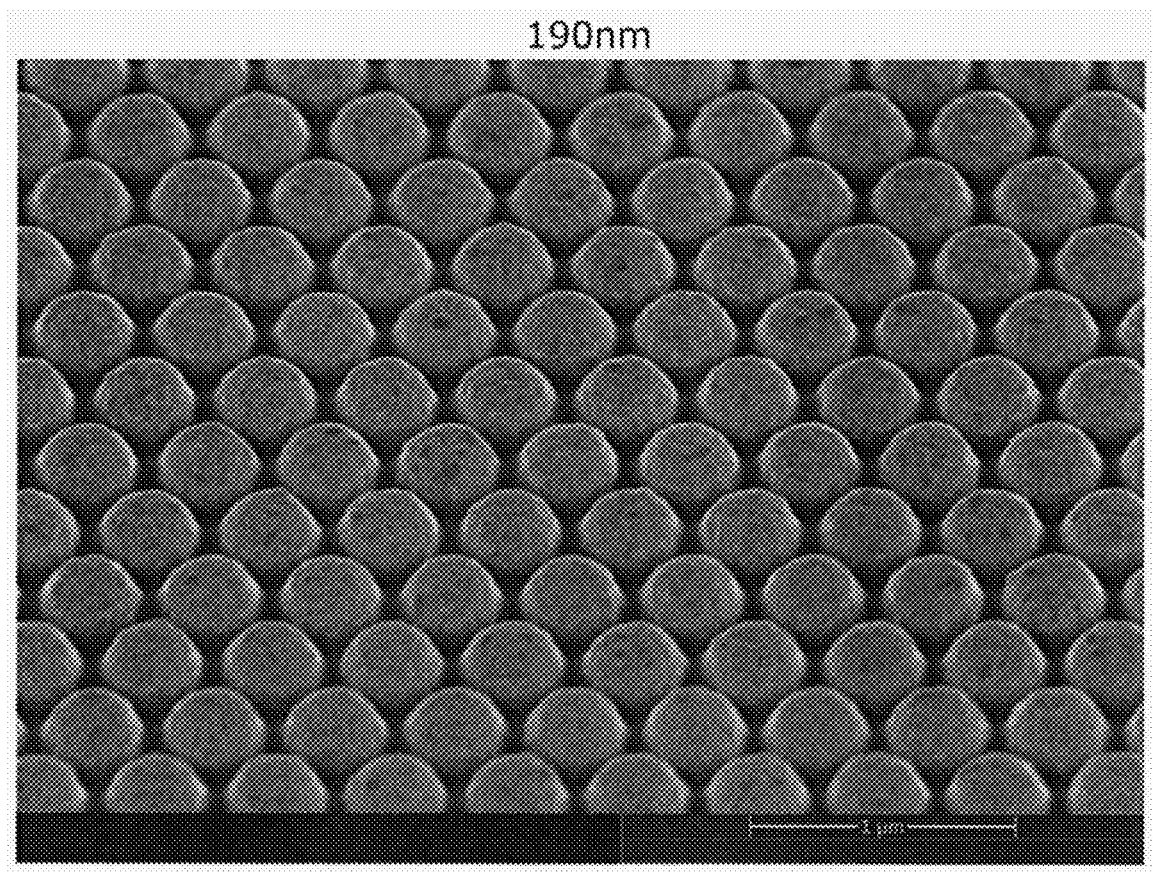
FIG. 8A is a view showing a perspective SEM image of the metal microstructure of Experimental Example A.
Figure 8B:
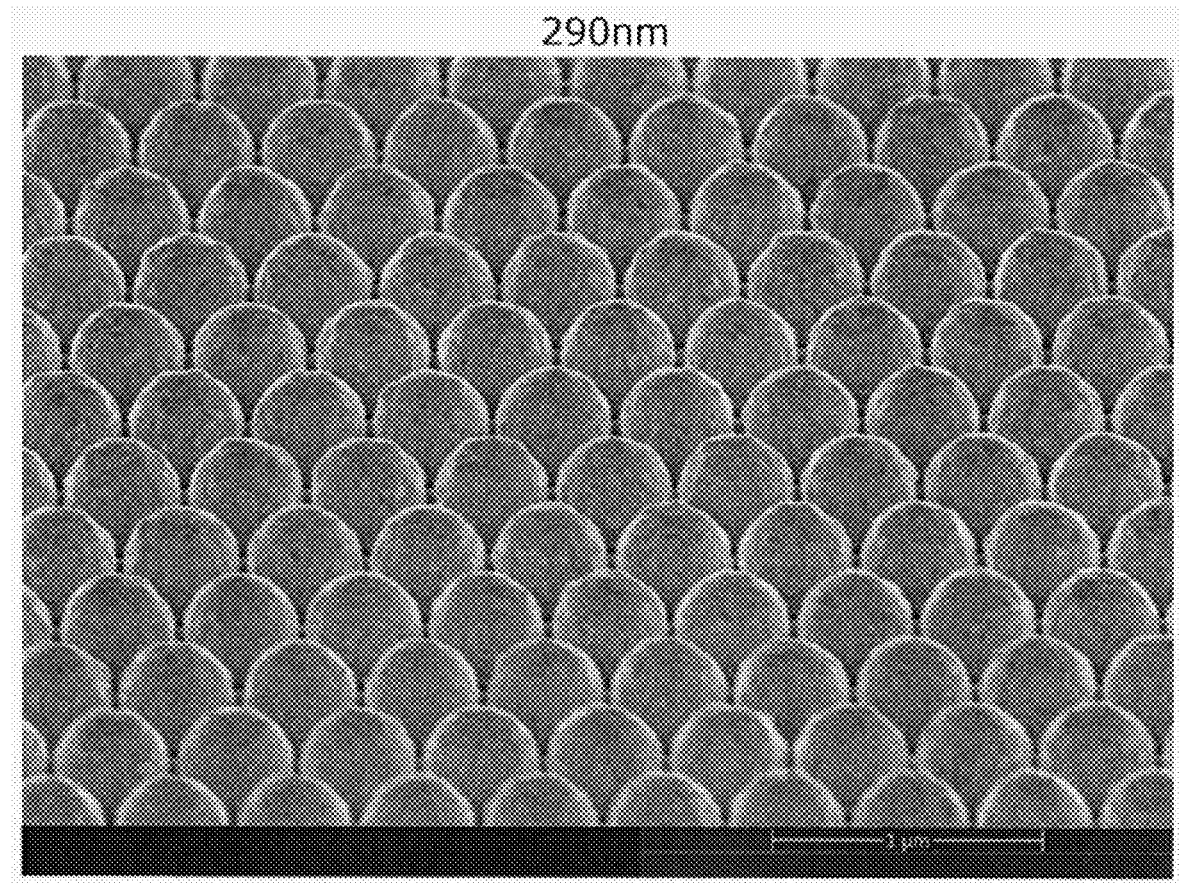
FIG. 8B is a view showing a perspective SEM image of the metal microstructure of Experimental Example B.
Figure 8C:
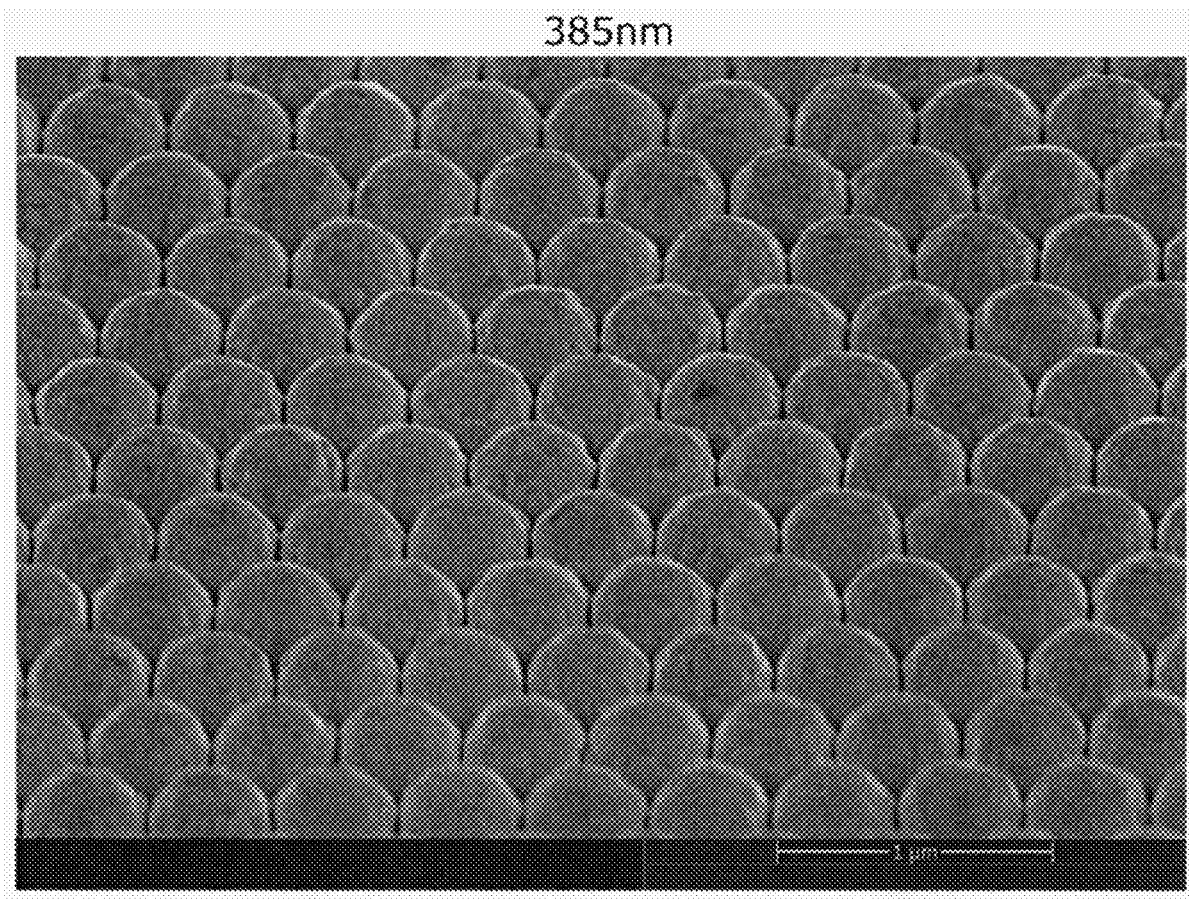
FIG. 8C is a view showing a perspective SEM image of the metal microstructure of Experimental Example C.
Figure 8D:
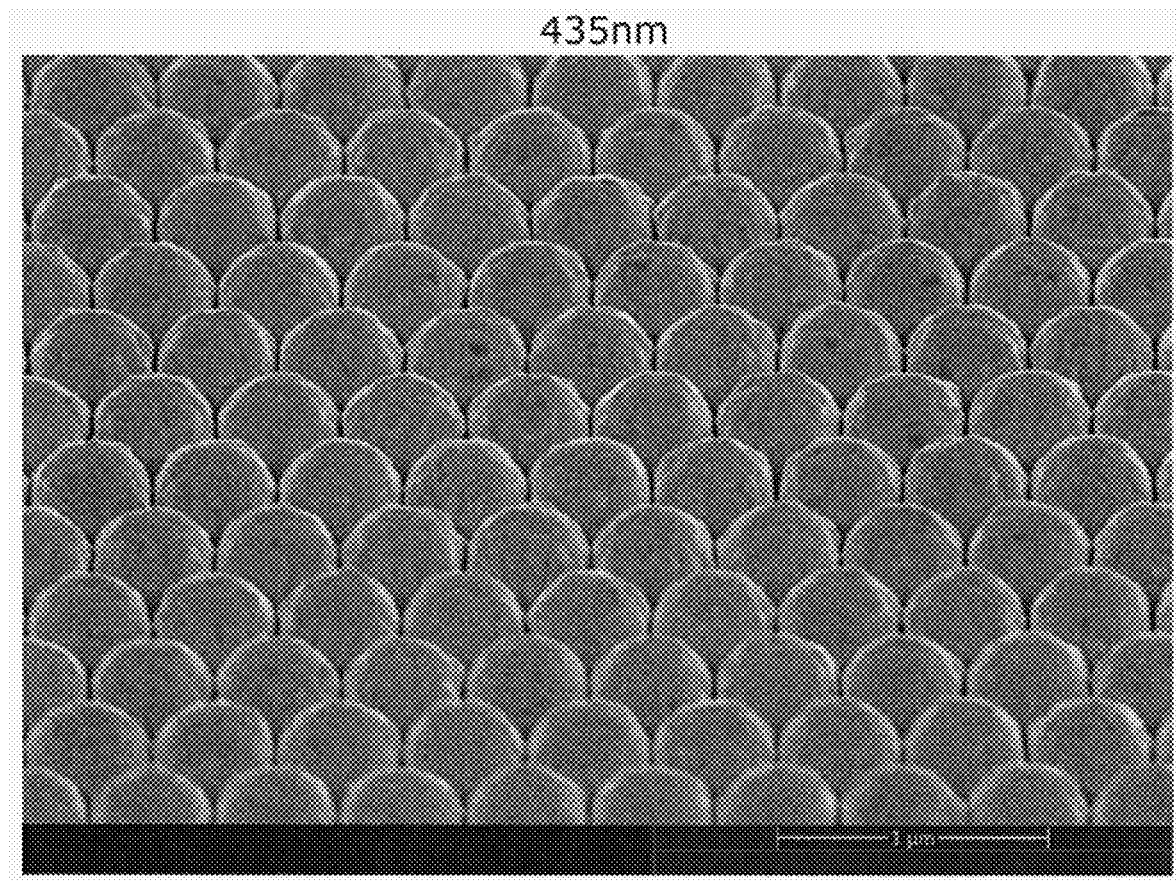
FIG. 8D is a view showing a perspective SEM image of the metal microstructure of Experimental Example D.
Figure 8E:
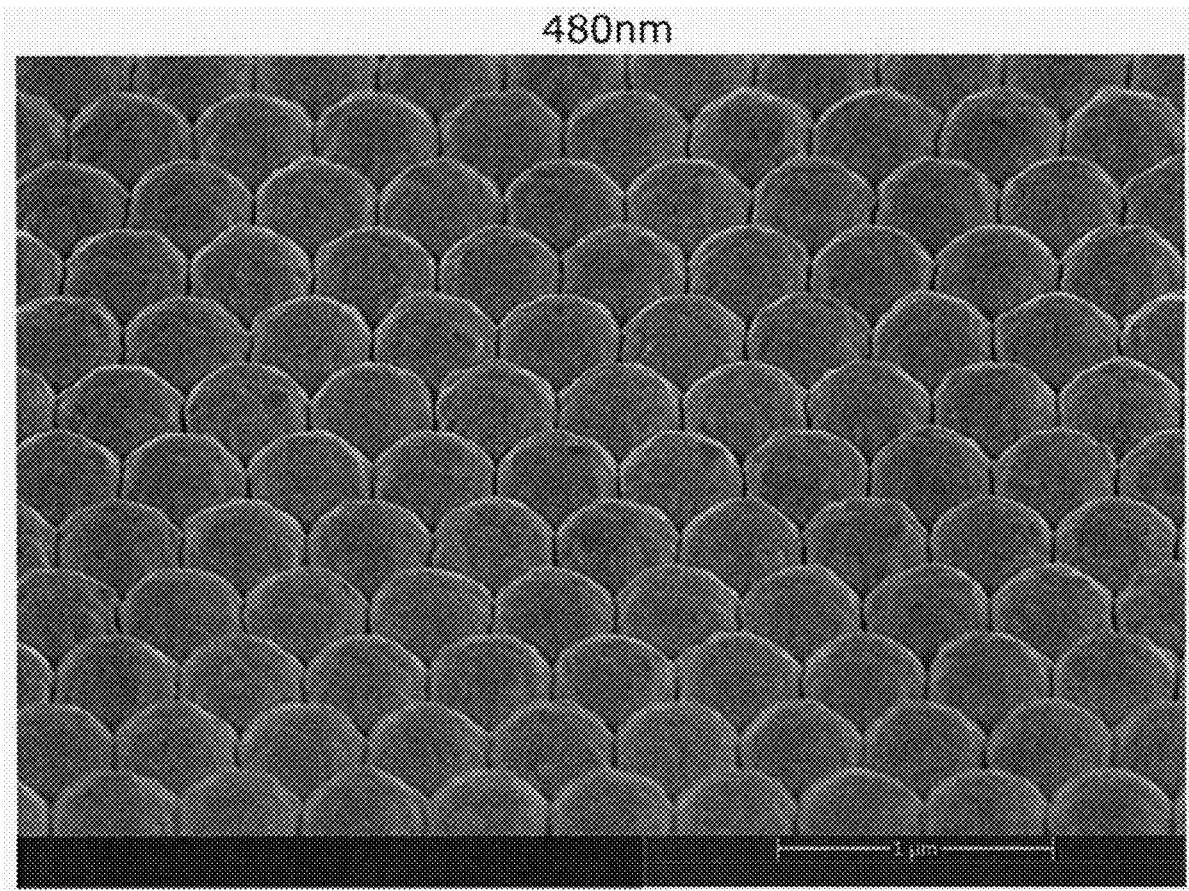
FIG. 8E is a view showing a perspective SEM image of the metal microstructure of Experimental Example E.

As shown in FIG. 8A, in Experimental Example A, the shape of each of the plurality of the protrusions forming the metal microstructure is a circular shape with rounded tops, and the gaps between the protrusions are wide.

As shown in FIGS. 8B to 8E, the gap between the plurality of the protrusions becomes narrower, as the protrusion Au film thickness increases. As described above, it is revealed that the shape of each of the plurality of the protrusions approaches a substantially hexagonal shape in a plan view.

FIGS. 9A to 9E are cross-sectional SEM images of the metal microstructures of Experimental Examples A to E, respectively. In these cross-sectional SEM images, in order to improve the visibility of the shape of the protrusion, the plurality of the protrusions 2043a are covered with a protective film and photographed.

FIGS. 9A to 9D, the bottom of the gap between the adjacent protrusions 2043a is positioned below each top of the plurality of the fine protrusions 2042a. Therefore, the depth A (see FIG. 4B) in the thickness direction of the sensor substrate in the gap present between the adjacent protrusions 2043a is larger than the radius of the imaginary circle.

Figure 9A:
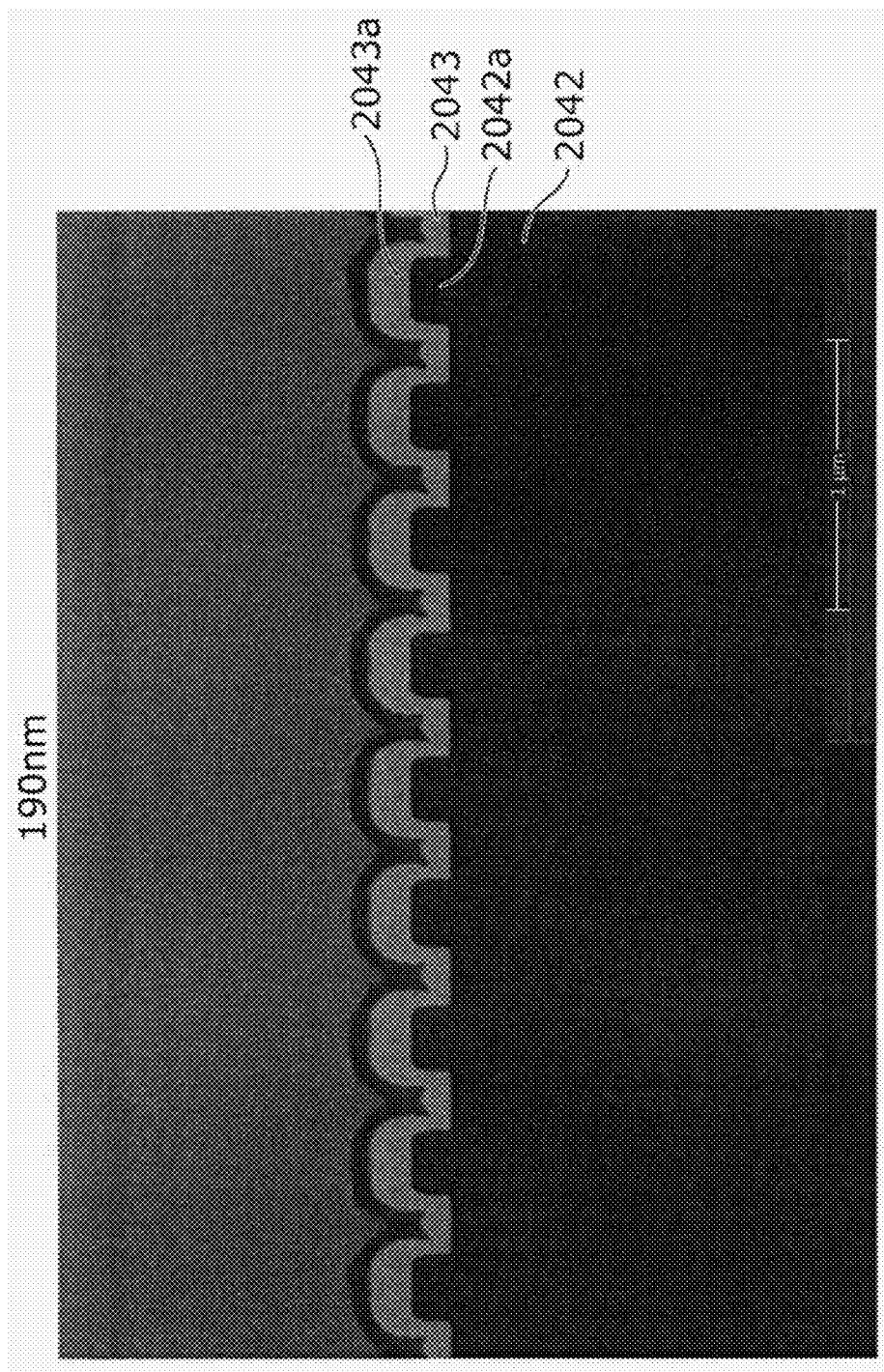
FIG. 9A is a diagram showing a cross-sectional SEM image of the metal microstructure of Experimental Example A.
Figure 9B:
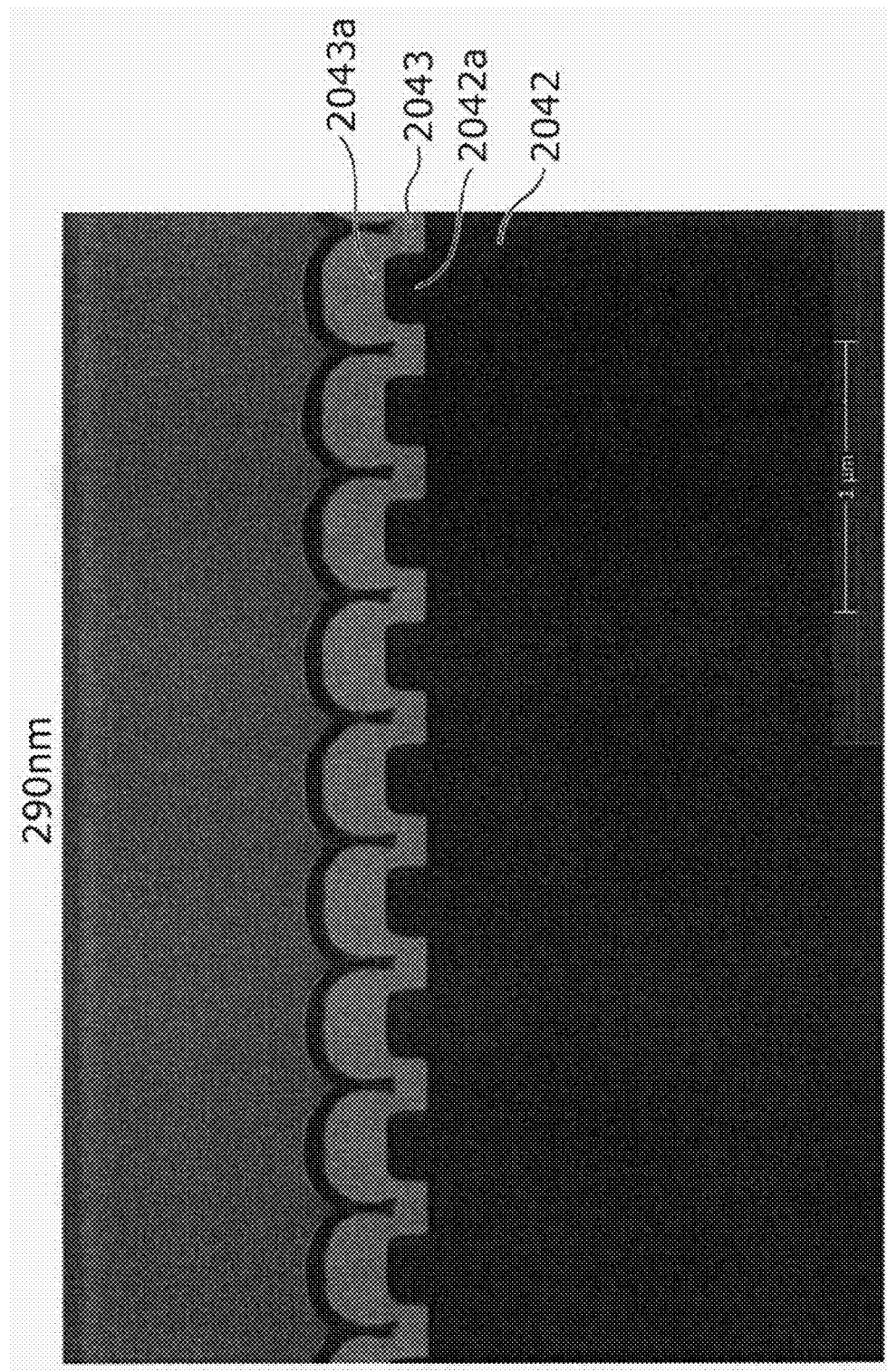
FIG. 9B is a diagram showing a cross-sectional SEM image of the metal microstructure of Experimental Example B.
Figure 9C:
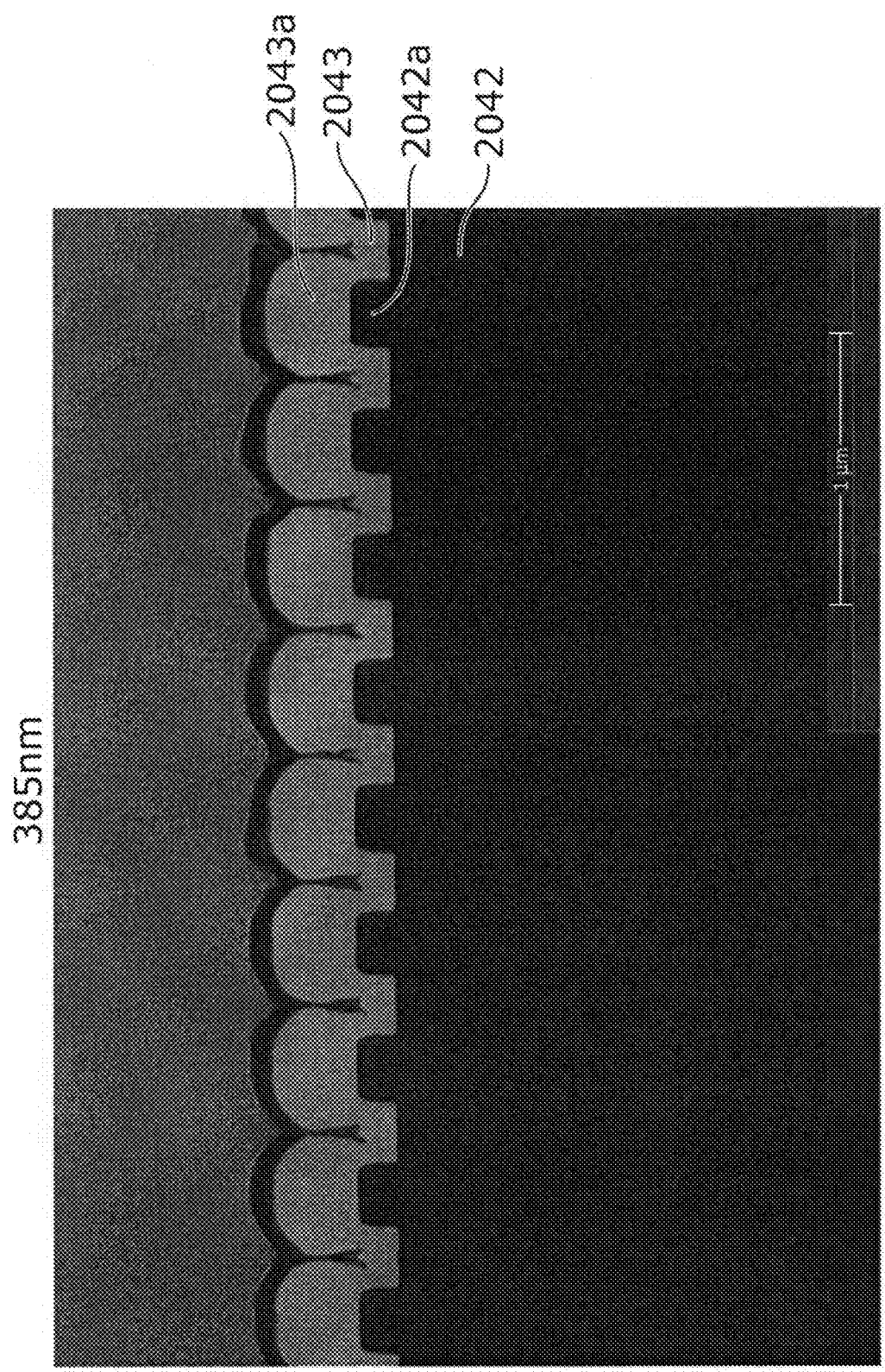
FIG. 9C is a diagram showing a cross-sectional SEM image of the metal microstructure of Experimental Example C.
Figure 9D:
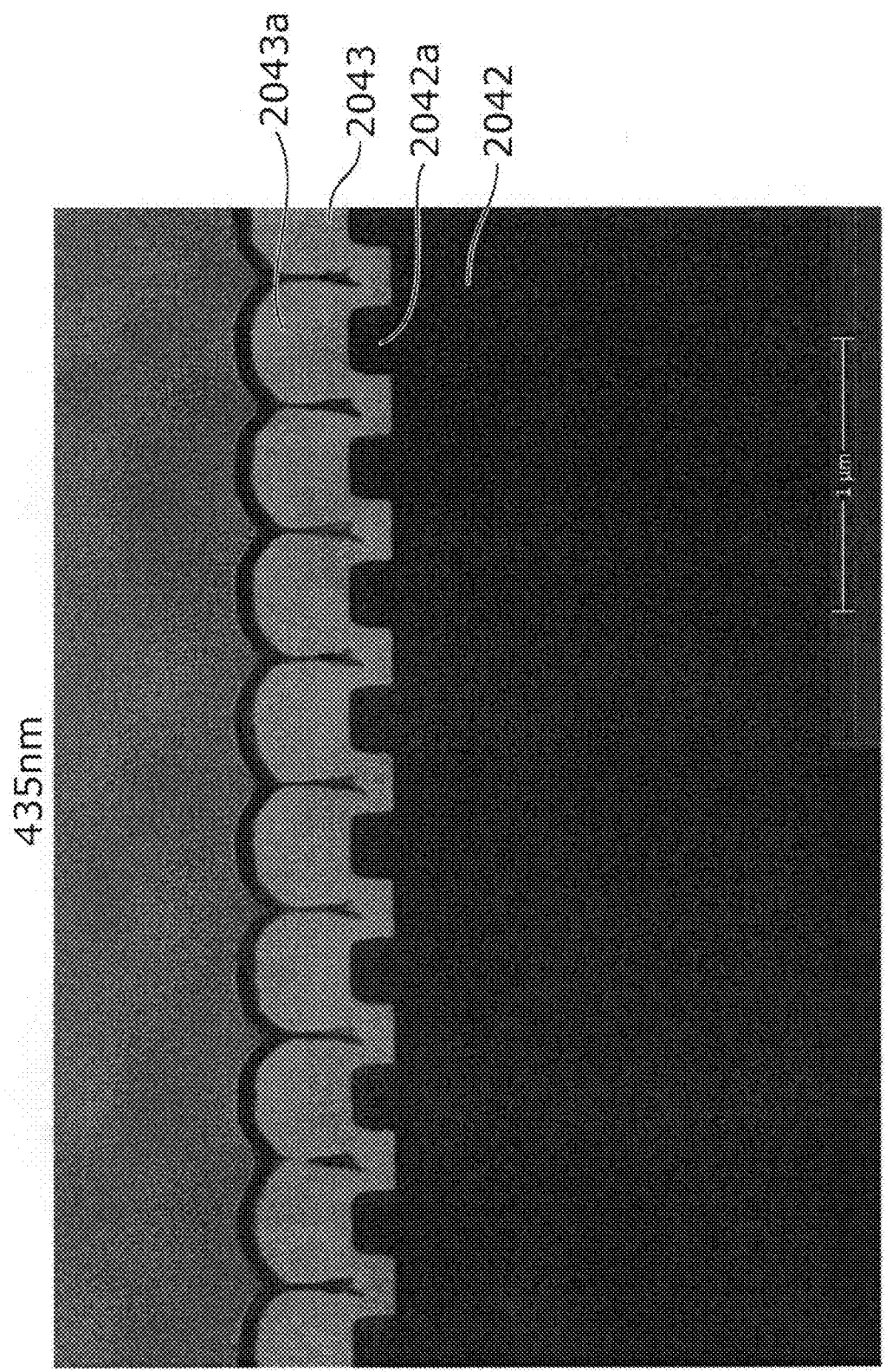
FIG. 9D is a diagram showing a cross-sectional SEM image of the metal microstructure of Experimental Example D.
Figure 9E:
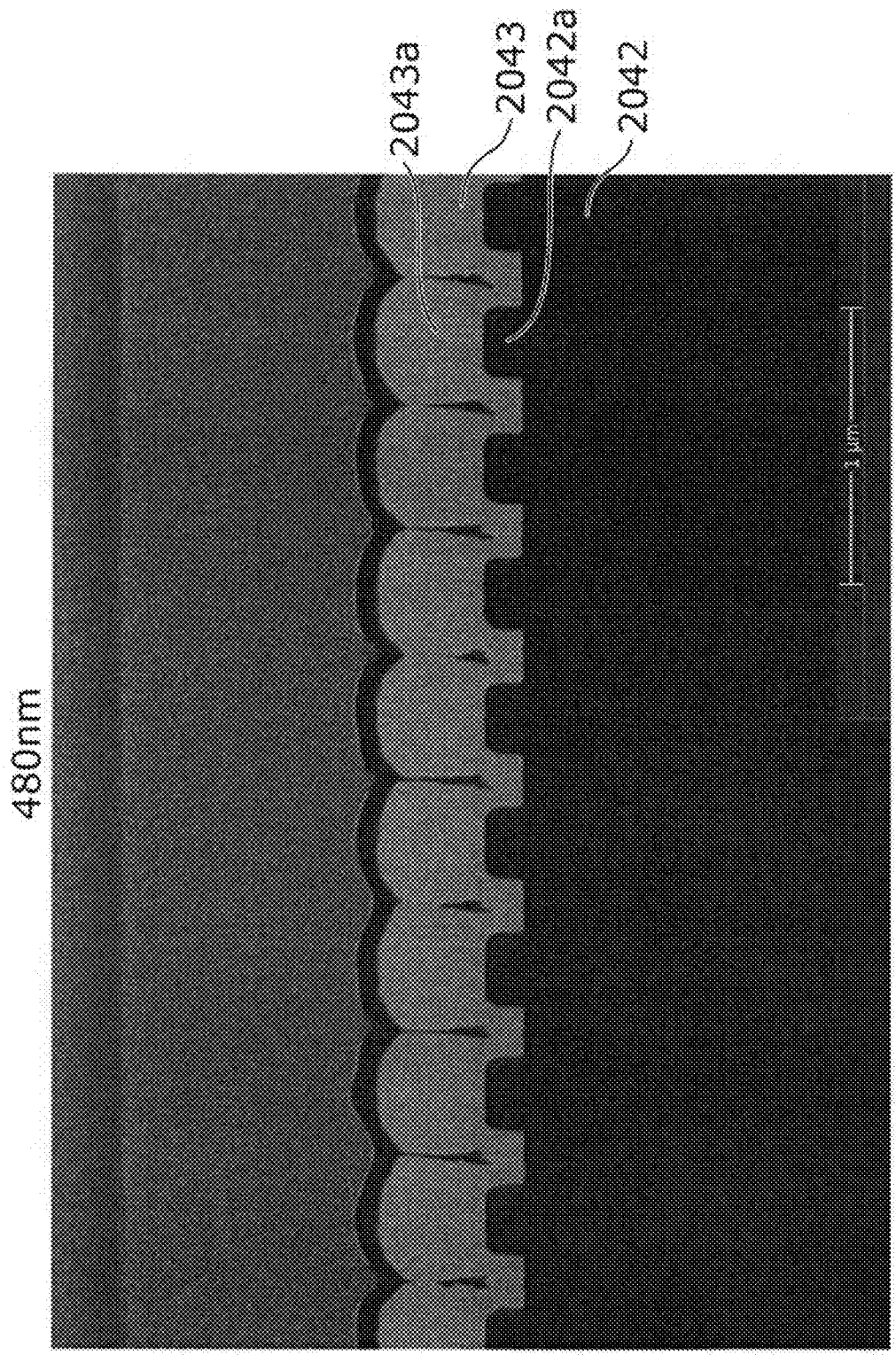
FIG. 9E is a diagram showing a cross-sectional SEM image of the metal microstructure of Experimental Example E.

On the other hand, in FIG. 9E, a contact part is generated between adjacent protrusions. Therefore, the bottom of the gap between the adjacent protrusions 2043a is located above each top of the plurality of the fine protrusions 2042a. Accordingly, the depth A (see FIG. 4B) in the thickness direction of the sensor substrate in the gap between the adjacent protrusions 2043a is smaller than the radius of the imaginary circle.

In the metal microstructure in the present disclosure, the gap between the plurality of the protrusions 2043a becomes narrower, as the protrusion Au film thickness increases. In the metal microstructure of Experimental Example A shown in FIG. 9A, the minimum width of the gap between the adjacent protrusions 2043a was about 90 nm. In the metal microstructure of Experimental Example B shown in FIG. 9B, the minimum width of the gap between adjacent protrusions 2043a was about 40 nm. In the metal microstructure of Experimental Example C shown in FIG. 9C, the minimum width of the gap between the adjacent protrusions 2043a was about 20 nm. In the metal microstructure of Experimental Example D shown in FIG. 9D, the minimum width of the gap between the adjacent protrusions 2043a was about 15 nm, and some of the protrusions were in contact with each other and there was no gap. In addition, in the metal microstructure of Experimental Example E shown in FIG. 9E, although there were several gaps each having a minimum width of about 10 nm, many of the protrusions were in contact with each other and no gap was present therebetween.

The gap is preferably as narrow as possible from the viewpoint of electric field enhancement. However, if the gap is too small, a part where adjacent metal microstructures come into contact with each other is formed. If the contact part is present in the gap, the desired plasmon resonance cannot be provided in the gap, and as a result, the light emission enhancement per unit area is decreased. Therefore, in order not to decrease the light emission intensity per unit area, it is preferable to narrow the gap while suppressing an increase in the number of contact parts.

In addition, in a case where the sensor substrate according to the present disclosure is used as a virus sensor using a sandwich assay, the sensor substrate having the metal microstructure on which the first antibody having a property of binding specifically to the analyte, for example, a virus nucleoprotein (NP), has been immobilized is used. In the sandwich assay, the NP is bound to the first antibody (hereinafter, referred to as immobilized antibody) immobilized on the SAM on the surface of the metal microstructure, and then, the NP is bound to the second antibody (hereinafter, labeled antibody) which has a property of binding specifically to the NP and is labeled with a fluorescent substance. In this way, a composite of the immobilized antibody/the NP/the labeled antibody is formed. In a case where the NP is a nucleoprotein of an influenza virus and where VHH antibodies are used as an immobilized antibody and a labeled antibody, since the size of each of the immobilized antibody, the NP, and the labeled antibody is 5 nm, the size of the composite is 15 nm. In a case where the composite provided by a sandwich assay is present in the gap between adjacent protrusions, which is the maximum electric field enhancement region, the strongest light emission is provided, since the gap is the strongest electric field enhancement region in the metal microstructure. Therefore, the minimum width of the gap is preferably not less than 15 nm. From the above, it is preferable that the nanogap is not less than 15 nm and as narrow as possible. In other words, in the metal microstructure of Experimental Example C shown in FIG. 9C, since the minimum width of the gap is 20 nm, the maximum light emission enhancement would be provided most desirably.

Although not shown, when the metal microstructure was irradiated with excitation light having a wavelength of 785 nm, plasmon resonance occurred on the surface of the metal microstructure and fluorescence having a wavelength of 800 nm was emitted from the fluorescent substance forming the composite. In this metal microstructure, a precipitous absorption peak due to plasmon resonance was observed in the wavelength band of 650 nm to 850 nm.

[Formation of SAM and Immobilization of Immobilized Antibody]

In a case where the sensor substrate is used as a virus sensor, a SAM through which the immobilized antibody has been immobilized on the surface of the metal microstructure is formed. Here, the SAM was formed on the metal microstructure by immersing the sensor substrate produced by the above method in a SAM solution overnight in an incubator of 40 degrees Celsius.

The SAM solution was prepared by the following procedure. Carboxy-EG6-undecanethiol and Hydroxy-EG3-undecanethiol were each diluted with ethanol and mixed. The provided mixed material was diluted with ethanol to prepare the SAM solution.

As the first VHH antibody and the second VHH antibody, alpaca-derived VHH antibodies capable of binding specifically to a nucleoprotein of an influenza virus were prepared.

Thereafter, the carboxyl group (COOH) end of the SAM and the amino group ($NH_2$) end of the first VHH antibody were bound by an EDC-NHS reaction to form a peptide. In this way, the first VHH antibody was immobilized on the SAM.

[Detection of Analyte]

A nucleoprotein (NP) of an influenza virus, which was an analyte, was bound to the immobilized first VHH antibody, and further the second VHH antibody labeled with an organic fluorescent dye (light emission wavelength: 800 nm), which was a fluorescent substance, was bound to the NP to conduct a sandwich assay.

The sample provided by the sandwich assay was irradiated with a laser beam having a wavelength of 785 nm to excite the organic fluorescent dye of the composite contained in the sample, and the intensity of the fluorescence having a wavelength of 800 nm emitted from the organic fluorescent dye was measured.

Figure 10:
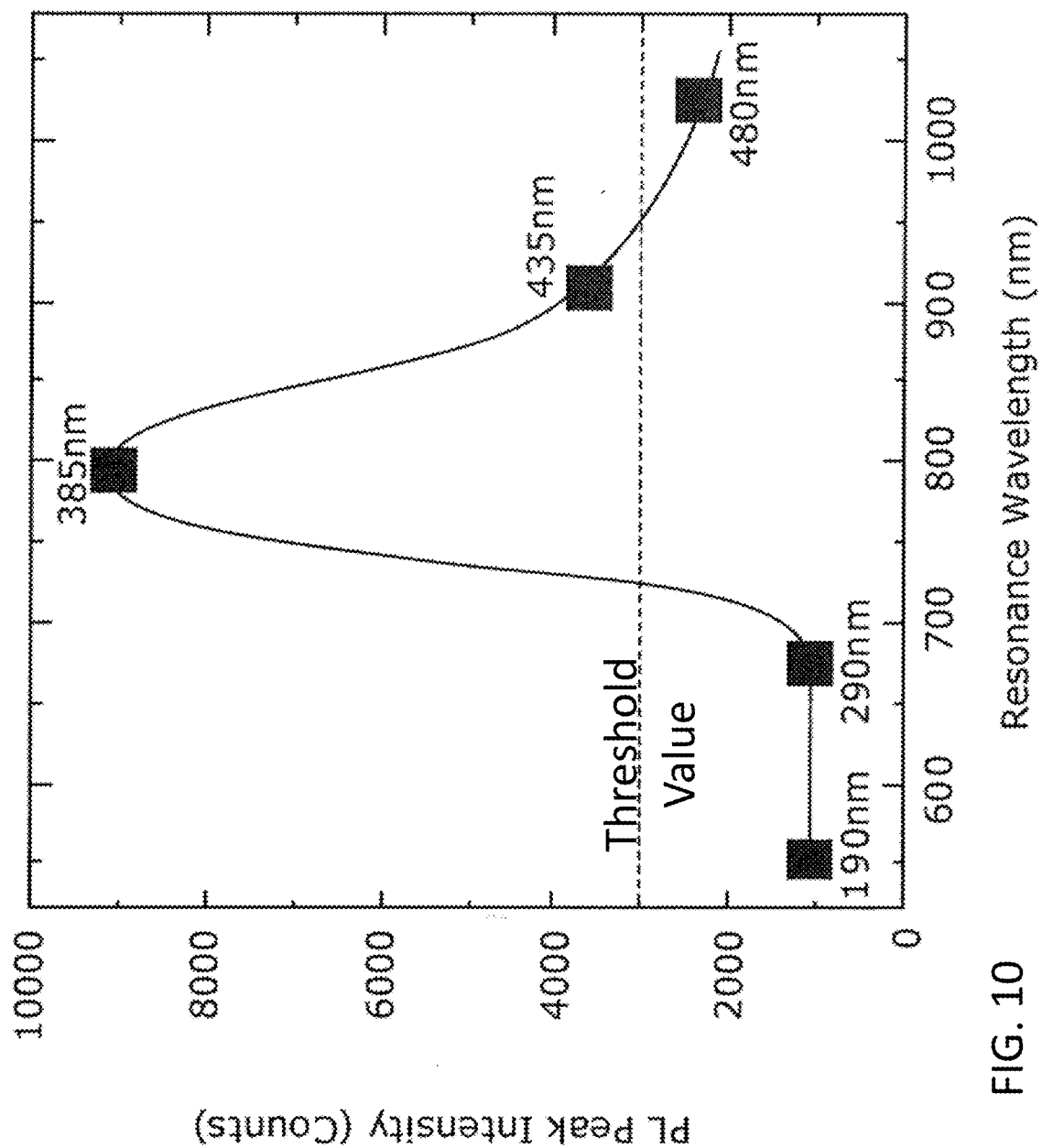
FIG. 10 is a graph showing fluorescence intensity depending on a difference in a protrusion Au film thickness of the metal microstructure in a case where the sensor substrate is used for a virus sensor.

FIG. 10 is a graph showing the fluorescence intensity depending on the difference in a protrusion Au film thickness of the metal microstructure in a case where the sensor substrate is used for a virus sensor. The same amounts of NP and labeled antibody were introduced into five sensor substrates having different protrusion Au film thicknesses, and a sandwich assay was performed. In the present disclosure, if the fluorescence intensity was not less than 3000 counts, the threshold value was set to 3000 counts, since the desired detection sensitivity is provided. At this time, the protrusion Au film thickness is within a range of not less than 310 nm to not more than 460 m.

As described above, in the sensor substrates having the metal microstructures of Experimental Examples A and B, the shape of each of the plurality of the protrusions is a circular shape in a plan view. In the metal microstructures of Experimental Examples A and B, the minimum width of the gap between the adjacent protrusions is about 90 nm and about 40 nm, respectively. For this reason, the electric field enhancement is small. As a result, as shown in FIG. 10, these two sensor substrates have low fluorescence intensity.

On the other hand, in the sensor substrate having the metal microstructure of Experimental Example C, the maximum fluorescence intensity has been provided. At this time, the minimum width of the gap between the adjacent protrusions was about 20 nm. As described above, the size of the composite of the immobilized antibody/the NP/the labeled antibody provided by the sandwich assay is 15 nm. Therefore, if the minimum width of the gap is about 20 nm, the composite provided by the sandwich assay can be present in the gap which is the maximum electric field enhancement region, so that the strongest fluorescence enhancement is provided.

In addition, the fluorescence intensity of the sensor substrate having the metal microstructure of Experimental Example D is lower than that of the sensor substrate having the metal microstructure of Experimental Example C. At this time, since the minimum width of the gap between the adjacent protrusions is equal to or less than the size of the composite (15 nm), the composite is less likely to enter a part below the minimum width of the gap, compared to the case where the minimum width of the gap is larger than the size of the composite. Therefore, it is conceivable that the fluorescence intensity is lower in the present case than in the case of Experimental Example C. However, the fluorescence intensity is about 3600 counts, and the fluorescence intensity equal to or higher than the threshold value has been provided.

In addition, the fluorescence intensity of the sensor substrate having the metal microstructure of Experimental Example E is further lower than that of the sensor substrate having the metal microstructure of Experimental Example D. From the cross-sectional SEM images of FIGS. 9D and 9E, since the number of the contact part where the adjacent protrusions contact each other in the metal microstructure of Experimental Example E is greater than in the metal microstructure of Experimental Example D, the light emission intensity per unit area is decreased. Therefore, it is conceivable that the fluorescence intensity was further decreased, compared to the sensor substrate having the metal microstructure of Experimental Example D. At this time, the fluorescence intensity is about 2200 counts, and the fluorescence intensity is lower than the threshold value.

As described above, the sensor substrate, the manufacturing method of the sensor substrate, and the detection device according to the present disclosure have been described based on the embodiments and the experimental examples. However, the present disclosure is not limited to the embodiments and the experimental examples. Without departure from the gist of the present disclosure, various modifications conceived by those skilled in the art would be made in the embodiments and experimental examples. Other forms constructed by combining a part of configuration elements in the embodiments and experimental examples would be made. Such various modifications or forms are included in the scope of this disclosure.

In the above-described embodiment, a configuration in which one sensor device 202 includes one sensor cell 204 has been described; however, one sensor device 202 may include a plurality of sensor cells 204. In the above embodiment, the sensor device 202 has a rectangular shape. However, the sensor device 202 may have a circular shape such as a CD. Thereby, a plurality of detections can be easily performed with one sensor device 202.

In the above embodiment, the SAM 2044 has been formed on the metal microstructure 2041; however, the SAM 2044 is not necessarily formed. In other words, the SAM 2044 does not have to be formed on the metal film 2043.

In the above embodiment, the detection device 200 detects the surface-enhanced fluorescence using the beam splitter 210 and the lens 212; however, the detection device is not limited to this configuration.

In the above-described embodiment, the example in which both the wavelength of the excitation light and the wavelength of the fluorescence are included in one absorption region has been described. However, the wavelength of the excitation light and the wavelength of the fluorescence wavelength may be individually included in the two absorption regions. Even in this case, surface plasmon can be generated efficiently and fluorescence can be effectively enhanced.

INDUSTRIAL APPLICABILITY

The sensor substrate according to the present disclosure is a surface plasmon sensor substrate used in, for example, a light emission enhanced fluorescence method, and can be used for a virus sensor or the like. The sensor substrate, the manufacturing method of the sensor substrate, and the detection device according to the present disclosure can be used for a detection system for detecting concentration of a virus floating in a room with high sensitivity in order to lower an infection risk of virus to a person staying in the room.

REFERENTIAL SIGNS LIST

10 Detection system
100 Collection device
102 Suction device
104 Collection liquid tank
106, 114 Pump
108 Cyclone
110 Air suction opening 112 Cleaning liquid tank
120 Waste liquid tank
122 Liquid channel
200 Detection device
202 Sensor device
204 Sensor cell
204a Flow path
204b Sensor substrate
206 Introduction part
208 Light source
210 Beam splitter
212 Lens
214 Detection part
2041 Metal microstructure
2042 Resin substrate
2042a Fine protrusion
2043 Metal film
2043a Protrusion
2044 SAM
2045 First VHH antibody
2061 Sample liquid
2062 Virus (Analyte)
2063 Second VHH antibody
2064 Fluorescent substance
L Outline
M Imaginary circle
V Imaginary line

The invention claimed is:

1. A sensor substrate comprising:
a metal microstructure for generating surface plasmon when irradiated with excitation light, wherein:
the metal microstructure is composed of a plurality of protrusions comprising a plurality of fine protrusions protruding from a substrate in a normal direction of an upper surface of the substrate and a metal film disposed over the plurality of fine protrusions;
each of the plurality of the protrusions has a substantially hexagonal shape in plan view and the plurality of the protrusions are arranged in a matrix such that the plurality of protrusions having the hexagonal shape forms a honeycomb shape in a plan view,
when a circle is drawn to be inscribed in a hexagon forming the honeycomb shape, a depth in the normal direction of a gap present between adjacent protrusions of the plurality of protrusions is larger than a radius of the circle,
a thickness of the metal film measured at a top of each of the plurality of fine protrusions is not less than 1.6 times and not more than 2.3 times as thick as a height of each of the plurality of fine protrusions,
a minimum width of the gap present between the adjacent protrusions is more than 10 nm and less than 40 nm,
the substrate and the plurality of fine protrusions are made of resin, and
the thickness of the metal film measured at the top of each of the plurality of fine protrusions is not less than 310 nm and not more than 460 nm at the top of the plurality of fine protrusions.

2. The sensor substrate according to claim 1, wherein the plurality of protrusions having substantially hexagonal shape have an area of 80% or more of an area of the hexagon forming the honeycomb shape.

3. The sensor substrate according to claim 1, wherein a depth of the gap in the normal direction is not less than 380 nm and not more than 510 nm.

4. The sensor substrate according to claim 1, wherein a bottom of the gap is located below the top of each of the plurality of fine protrusions.

5. The sensor substrate according to claim 1, wherein:
each of the plurality of fine protrusions is a cylinder having a diameter of not less than 140 nm and not more than 400 nm and a height of not less than 125 nm and not more than 225 nm, and
the plurality of fine protrusions are arranged to have a pitch of not less than 280 nm and not more than 520 nm.

6. A detection device comprising:
the sensor substrate according to claim 1;
wherein
a first antibody having a property of binding specifically to an analyte is immobilized on the metal microstructure of the sensor substrate;
the detection device further comprises:
an introduction opening through which a second antibody and a sample pass to the metal microstructure; wherein the second antibody has a property of binding specifically to the analyte and is labeled with a fluorescent substance, and wherein the sample may include the analyte;
a light irradiation part for irradiating the metal microstructure to which the second antibody and the sample has been introduced with the excitation light; and
a detection part which detects the analyte based on fluorescence generated from the fluorescent substance by the irradiation with the excitation light.

7. A manufacturing method of the sensor substrate according to claim 1, the method comprising:
preparing the substrate having the plurality of fine protrusions; and
forming the metal film on the substrate to form the sensor substrate comprising the metal microstructure having the plurality of protrusions,
wherein the substrate is made of resin.

8. The manufacturing method of the sensor substrate according to claim 7, wherein
each of the plurality of fine protrusions has a cylindrical shape.

* * * * *